(12) United States Patent
Kloke

(10) Patent No.: US 10,898,446 B2
(45) Date of Patent: Jan. 26, 2021

(54) DELIVERY OF HYDROPHOBIC ACTIVE AGENTS FROM HYDROPHILIC POLYETHER BLOCK AMIDE COPOLYMER SURFACES

(71) Applicant: Surmodics, Inc., Eden Prairie, MN (US)

(72) Inventor: Timothy M. Kloke, Victoria, MN (US)

(73) Assignee: Surmodics, Inc., Eden Prairie, MN (US)

(*) Notice: Subject to any disclaimer, the term of this patent is extended or adjusted under 35 U.S.C. 154(b) by 0 days.

(21) Appl. No.: 15/840,540

(22) Filed: Dec. 13, 2017

(65) Prior Publication Data

US 2018/0169032 A1    Jun. 21, 2018

Related U.S. Application Data

(60) Provisional application No. 62/436,694, filed on Dec. 20, 2016.

(51) Int. Cl.
*A61K 9/70* (2006.01)
*A61L 29/16* (2006.01)
(Continued)

(52) U.S. Cl.
CPC .......... *A61K 9/7007* (2013.01); *A61K 31/337* (2013.01); *A61K 31/436* (2013.01);
(Continued)

(58) Field of Classification Search
None
See application file for complete search history.

(56) References Cited

U.S. PATENT DOCUMENTS

| | | |
|---|---|---|
| 3,389,099 A | 6/1968 | Dressler et al. |
| 3,936,391 A | 2/1976 | Gabby et al. |

(Continued)

FOREIGN PATENT DOCUMENTS

| | | |
|---|---|---|
| CA | 2836266 | 11/2012 |
| CA | 2760187 | 1/2018 |

(Continued)

OTHER PUBLICATIONS

Product Data Sheet for Pebax® MV 1074 SA 01 MED from Arkema (2013, pp. 1-2). (Year: 2013).*

(Continued)

*Primary Examiner* — Aradhana Sasan
(74) *Attorney, Agent, or Firm* — Pauly, DeVries Smith & Deffner LLC

(57) ABSTRACT

Embodiments of the invention include drug delivery coatings and devices including the same. In an embodiment, a drug delivery coating is included herein having a base polymeric layer, the base polymeric layer including a hydrophilic polyether block amide copolymer and having a hydrophilic surface. The drug delivery coating can further include a therapeutic agent layer forming an exterior surface the drug delivery coating, the therapeutic agent layer contacting the hydrophilic surface of the base polymeric layer and having a composition different than the base polymeric layer, the therapeutic agent layer including a particulate hydrophobic therapeutic agent and a cationic agent. Other embodiments are also included herein.

18 Claims, 5 Drawing Sheets

(51) Int. Cl.

| | | |
|---|---|---|
| *A61L 29/08* | (2006.01) | |
| *A61L 31/10* | (2006.01) | |
| *A61L 31/16* | (2006.01) | |
| *A61L 27/34* | (2006.01) | |
| *A61K 31/337* | (2006.01) | |
| *A61K 31/436* | (2006.01) | |
| *A61K 47/34* | (2017.01) | |
| *A61K 47/32* | (2006.01) | |
| *A61L 27/54* | (2006.01) | |

(52) U.S. Cl.
CPC .............. *A61K 47/32* (2013.01); *A61K 47/34* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *A61L 2300/416* (2013.01); *A61L 2300/608* (2013.01); *A61L 2300/63* (2013.01); *A61L 2420/02* (2013.01); *A61L 2420/08* (2013.01)

(56) References Cited

U.S. PATENT DOCUMENTS

| | | |
|---|---|---|
| 4,195,637 A | 4/1980 | Gruntzig et al. |
| 4,456,627 A | 6/1984 | Van Heteren |
| 4,490,421 A | 12/1984 | Levy |
| 4,638,045 A | 1/1987 | Kohn et al. |
| 4,722,906 A | 2/1988 | Guire |
| 4,973,493 A | 11/1990 | Guire |
| 4,979,959 A | 12/1990 | Guire |
| 5,002,582 A | 3/1991 | Guire et al. |
| 5,041,089 A | 8/1991 | Mueller et al. |
| 5,073,641 A | 12/1991 | Bundgaard et al. |
| 5,087,246 A | 2/1992 | Smith |
| 5,102,402 A | 4/1992 | Dror et al. |
| 5,201,753 A | 4/1993 | Lampropoulos et al. |
| 5,263,992 A | 11/1993 | Guire |
| 5,297,607 A | 3/1994 | Beauchamp |
| 5,304,121 A | 4/1994 | Sahatjian |
| 5,318,587 A | 6/1994 | Davey |
| 5,334,146 A | 8/1994 | Ozasa |
| 5,382,234 A | 1/1995 | Cornelius et al. |
| 5,397,307 A | 3/1995 | Goodin |
| 5,414,075 A | 5/1995 | Swan et al. |
| 5,466,719 A | 11/1995 | Jakobson et al. |
| 5,502,219 A | 3/1996 | Harris |
| 5,512,329 A | 4/1996 | Guire et al. |
| 5,556,383 A | 9/1996 | Wang et al. |
| 5,558,642 A | 9/1996 | Schweich, Jr. et al. |
| 5,571,089 A | 11/1996 | Crocker |
| 5,585,506 A | 12/1996 | Harvey |
| 5,616,608 A | 4/1997 | Kinsella et al. |
| 5,632,773 A | 5/1997 | Graham et al. |
| 5,637,460 A | 6/1997 | Swan et al. |
| 5,714,360 A | 2/1998 | Swan et al. |
| 5,728,732 A | 3/1998 | Corey |
| 5,741,551 A | 4/1998 | Guire et al. |
| 5,776,101 A | 7/1998 | Goy |
| 5,807,331 A | 9/1998 | Den Heijer et al. |
| 5,811,447 A | 9/1998 | Kunz et al. |
| 5,833,657 A | 11/1998 | Reinhardt et al. |
| 5,858,653 A | 1/1999 | Duran et al. |
| 5,882,336 A | 3/1999 | Janacek |
| 5,891,451 A | 4/1999 | Guerrero et al. |
| 5,980,948 A | 11/1999 | Goedemoed et al. |
| 6,007,833 A | 12/1999 | Chudzik et al. |
| 6,077,698 A | 6/2000 | Swan et al. |
| 6,168,748 B1 | 1/2001 | Wang et al. |
| 6,177,522 B1 | 1/2001 | Brady et al. |
| 6,210,364 B1 | 4/2001 | Anderson et al. |
| 6,278,018 B1 | 8/2001 | Swan |
| 6,299,604 B1 | 10/2001 | Ragheb et al. |
| 6,328,710 B1 | 12/2001 | Wang et al. |
| 6,340,465 B1 | 1/2002 | Hsu et al. |
| 6,394,995 B1 | 5/2002 | Solar et al. |
| 6,436,440 B1 | 8/2002 | Meffert et al. |
| 6,444,324 B1 | 9/2002 | Yang et al. |
| 6,465,178 B2 | 10/2002 | Chappa et al. |
| 6,482,348 B1 | 11/2002 | Wang et al. |
| 6,506,411 B2 | 1/2003 | Hunter et al. |
| 6,506,895 B2 | 1/2003 | Guire et al. |
| 6,514,734 B1 | 2/2003 | Clapper et al. |
| 6,515,009 B1 | 2/2003 | Kunz et al. |
| 6,517,515 B1 | 2/2003 | Eidenschink |
| 6,544,544 B2 | 4/2003 | Hunter et al. |
| 6,603,040 B1 | 8/2003 | Swan |
| 6,613,066 B1 | 9/2003 | Fukaya et al. |
| 6,620,904 B2 | 9/2003 | Lemke |
| 6,623,452 B2 | 9/2003 | Chien et al. |
| 6,623,504 B2 | 9/2003 | Vrba et al. |
| 6,663,662 B2 | 12/2003 | Pacetti et al. |
| 6,703,040 B2 | 3/2004 | Katsarava et al. |
| 6,730,064 B2 | 5/2004 | Ragheb et al. |
| 6,762,019 B2 | 7/2004 | Swan et al. |
| 6,896,842 B1 | 5/2005 | Hamilton et al. |
| 7,138,541 B2 | 11/2006 | Swan |
| 7,163,523 B2 | 1/2007 | Devens, Jr. et al. |
| 7,309,593 B2 | 12/2007 | Ofstead et al. |
| 7,348,055 B2 | 3/2008 | Chappa et al. |
| 7,438,710 B2 | 10/2008 | Anderson et al. |
| 7,507,469 B2 | 3/2009 | Yao et al. |
| 7,696,259 B2 | 4/2010 | Hanley et al. |
| 7,731,685 B2 | 6/2010 | Ragheb et al. |
| 7,736,689 B2 | 6/2010 | Chappa et al. |
| 7,758,892 B1 | 7/2010 | Chen et al. |
| 7,772,393 B2 | 8/2010 | Guire et al. |
| 7,797,033 B2 | 9/2010 | D'andrea et al. |
| 7,803,149 B2 | 9/2010 | Schaeffer et al. |
| 7,807,750 B2 | 10/2010 | Taton et al. |
| 7,820,193 B2 | 10/2010 | Hunter et al. |
| 7,850,727 B2 | 12/2010 | Shanley et al. |
| 8,034,765 B2 | 10/2011 | De et al. |
| 8,039,524 B2 | 10/2011 | Ralph et al. |
| 8,158,106 B2 | 4/2012 | Guire et al. |
| 8,172,793 B2 | 5/2012 | Choules et al. |
| 8,202,530 B2 | 6/2012 | Hossainy et al. |
| 8,246,576 B2 | 8/2012 | Slager |
| 8,257,305 B2 | 9/2012 | Speck et al. |
| 8,293,262 B2 | 10/2012 | Chen et al. |
| 8,439,868 B2 | 5/2013 | Speck et al. |
| 8,469,943 B2 | 6/2013 | Bates et al. |
| 8,487,137 B2 | 7/2013 | Guire et al. |
| 8,513,320 B2 | 8/2013 | Rooijmans |
| 8,557,272 B2 | 10/2013 | Zhao |
| 8,673,387 B2 | 3/2014 | Bates et al. |
| 8,697,112 B2 | 4/2014 | Ditizio et al. |
| 8,809,411 B2 | 8/2014 | Rooijmans |
| 8,871,819 B2 | 10/2014 | Meyering et al. |
| 8,889,760 B2 | 11/2014 | Kurdyumov et al. |
| 8,952,103 B2 | 2/2015 | Blondel et al. |
| 9,375,517 B2 | 6/2016 | Babcock |
| 9,555,119 B2 | 1/2017 | Ventura et al. |
| 9,757,497 B2 | 9/2017 | Slager |
| 9,861,727 B2 | 1/2018 | Slager et al. |
| 9,999,675 B2 | 6/2018 | Ventura et al. |
| 10,058,634 B2 | 8/2018 | Chappa et al. |
| 10,213,528 B2 | 2/2019 | Slager et al. |
| 10,213,529 B2 | 2/2019 | Slager |
| 10,617,793 B2 | 4/2020 | Slager et al. |
| 2002/0006493 A1 | 1/2002 | Chabrecek et al. |
| 2002/0123801 A1 | 9/2002 | Pacetti et al. |
| 2003/0065355 A1 | 4/2003 | Weber |
| 2003/0195611 A1 | 10/2003 | Greenhalgh et al. |
| 2003/0211135 A1 | 11/2003 | Greenhalgh et al. |
| 2004/0044404 A1 | 3/2004 | Stucke et al. |
| 2004/0051201 A1 | 3/2004 | Greenhalgh et al. |
| 2004/0105839 A1 | 6/2004 | Park |
| 2004/0117007 A1 | 6/2004 | Whitbourne et al. |
| 2005/0100580 A1 | 5/2005 | Osborne et al. |
| 2005/0187605 A1 | 8/2005 | Greenhalgh et al. |
| 2005/0255142 A1 | 11/2005 | Chudzik et al. |
| 2005/0281857 A1 | 12/2005 | Heyer et al. |
| 2006/0018948 A1 | 1/2006 | Guire et al. |

(56) References Cited

U.S. PATENT DOCUMENTS

| | | |
|---|---|---|
| 2006/0020243 A1 | 1/2006 | Speck et al. |
| 2006/0030669 A1 | 2/2006 | Taton et al. |
| 2006/0148982 A1 | 7/2006 | Uchegbu et al. |
| 2006/0200232 A1 | 9/2006 | Phaneuf et al. |
| 2006/0240194 A1 | 10/2006 | Lemke et al. |
| 2007/0026037 A1 | 2/2007 | Kloke et al. |
| 2007/0032882 A1 | 2/2007 | Lodhi et al. |
| 2007/0048351 A1 | 3/2007 | Lunn |
| 2007/0065481 A1 | 3/2007 | Chudzik et al. |
| 2007/0154591 A1 | 7/2007 | Andersen |
| 2007/0155906 A1 | 7/2007 | Hissink et al. |
| 2007/0218102 A1 | 9/2007 | Chudzik et al. |
| 2007/0224247 A1 | 9/2007 | Chudzik et al. |
| 2007/0260054 A1 | 11/2007 | Chudzik |
| 2008/0020013 A1 | 1/2008 | Reyes et al. |
| 2008/0220054 A1 | 9/2008 | Shastri et al. |
| 2008/0233183 A1 | 9/2008 | Mccook et al. |
| 2009/0030504 A1 | 1/2009 | Weber et al. |
| 2009/0043276 A1 | 2/2009 | Weber et al. |
| 2009/0043378 A1 | 2/2009 | Cheng et al. |
| 2009/0081276 A1 | 3/2009 | Alsberg et al. |
| 2009/0221767 A1 | 9/2009 | Malet |
| 2009/0226501 A1 | 9/2009 | Parsonage et al. |
| 2009/0227946 A1 | 9/2009 | Kangas |
| 2010/0015240 A1 | 1/2010 | Biggs |
| 2010/0040766 A1 | 2/2010 | Chappa et al. |
| 2010/0076377 A1 | 3/2010 | Ehrenreich et al. |
| 2010/0076401 A1 | 3/2010 | Von et al. |
| 2010/0087783 A1 | 4/2010 | Weber et al. |
| 2010/0096320 A1 | 4/2010 | Opperman et al. |
| 2010/0130837 A1 | 5/2010 | Matott |
| 2010/0198168 A1 | 8/2010 | Rooijmans |
| 2010/0272774 A1 | 10/2010 | Chappa |
| 2010/0274012 A1 | 10/2010 | Guire et al. |
| 2010/0292668 A1 | 11/2010 | Slager |
| 2011/0022027 A1 | 1/2011 | Morishita et al. |
| 2011/0046255 A1 | 2/2011 | Rooijmans |
| 2011/0059874 A1 | 3/2011 | Rooijmans et al. |
| 2011/0144373 A1 | 6/2011 | Swan et al. |
| 2011/0245367 A1 | 10/2011 | Kurdyumov et al. |
| 2011/0250255 A1 | 10/2011 | Parsonage et al. |
| 2011/0257339 A1 | 10/2011 | Fischer et al. |
| 2011/0275725 A1 | 11/2011 | Meyering et al. |
| 2012/0039983 A1 | 2/2012 | Uhrich et al. |
| 2012/0046384 A2 | 2/2012 | Kurdyumov et al. |
| 2012/0083734 A1 | 4/2012 | Ayres et al. |
| 2012/0148852 A1 | 6/2012 | Jelle et al. |
| 2012/0149934 A1 | 6/2012 | Kurdyumov |
| 2012/0177742 A1 | 7/2012 | Mcclain et al. |
| 2012/0177910 A1 | 7/2012 | Weber et al. |
| 2012/0296274 A1 | 11/2012 | Slager |
| 2013/0143056 A1 | 6/2013 | Swan et al. |
| 2013/0190689 A1 | 7/2013 | Slager |
| 2013/0197433 A1 | 8/2013 | Babcock |
| 2013/0302529 A1 | 11/2013 | Kurdyumov |
| 2014/0004158 A1 | 1/2014 | Mcgonigle |
| 2014/0142166 A1 | 5/2014 | Ventura |
| 2014/0162083 A1 | 6/2014 | Kurdyumov et al. |
| 2014/0193474 A1 | 7/2014 | Babcock et al. |
| 2014/0276636 A1* | 9/2014 | Lee ................. A61K 9/0024 604/517 |
| 2014/0336571 A1 | 11/2014 | Slager |
| 2015/0140107 A1 | 5/2015 | Slager et al. |
| 2015/0283092 A1 | 10/2015 | Ruddy et al. |
| 2017/0072057 A1 | 3/2017 | Ventura et al. |
| 2017/0112973 A1 | 4/2017 | Slager et al. |
| 2018/0110903 A1 | 4/2018 | Slager et al. |
| 2018/0272040 A1 | 9/2018 | Chappa et al. |

FOREIGN PATENT DOCUMENTS

| | | |
|---|---|---|
| CN | 1413118 | 4/2003 |
| CN | 1950114 | 4/2007 |
| CN | 1964750 | 5/2007 |
| CN | 104185661 | 8/2016 |
| CN | 103906505 | 1/2018 |
| EP | 0882461 | 12/1998 |
| EP | 1176993 | 6/2003 |
| EP | 1430917 | 6/2004 |
| EP | 1994950 | 11/2008 |
| EP | 1997525 | 12/2008 |
| EP | 2098230 | 6/2012 |
| EP | 2292225 | 6/2012 |
| EP | 2569023 | 10/2015 |
| EP | 2804915 | 3/2016 |
| EP | 2424581 | 3/2017 |
| JP | 2009502243 | 1/2009 |
| JP | 6140690 | 5/2017 |
| WO | 9964086 | 12/1999 |
| WO | 0110468 | 2/2001 |
| WO | 2001045742 | 6/2001 |
| WO | 03055611 | 7/2003 |
| WO | 2004017943 | 5/2004 |
| WO | 2005079754 | 9/2005 |
| WO | 2005113034 | 12/2005 |
| WO | 2006019848 | 2/2006 |
| WO | 2006026187 | 3/2006 |
| WO | 2006053175 | 5/2006 |
| WO | 2007012051 | 1/2007 |
| WO | 2007106441 | 9/2007 |
| WO | 2007136504 | 11/2007 |
| WO | 2009051614 | 4/2009 |
| WO | 2009113605 | 9/2009 |
| WO | 2009121629 | 10/2009 |
| WO | 2010111517 | 9/2010 |
| WO | 2010129328 | 11/2010 |
| WO | 2011005421 | 1/2011 |
| WO | 2011024831 | 3/2011 |
| WO | 2011052089 | 5/2011 |
| WO | 2011143237 | 11/2011 |
| WO | 2012003293 | 1/2012 |
| WO | 2012162061 | 11/2012 |
| WO | 2013109930 | 7/2013 |
| WO | 2013169879 | 11/2013 |
| WO | 2014071387 | 5/2014 |
| WO | 2014186729 | 11/2014 |
| WO | 2016123480 | 8/2016 |
| WO | 2018118671 | 6/2018 |

OTHER PUBLICATIONS

Akiyama, Yohko et al., "In Vitro and in Vivo evaluation of Mucoadhesive Microspheres Prepared for the Gastrointestinal Tract Using Polyglycerol Esters of Fatty Acids and a Poly(acrylic acid) Derivative," Pharmaceutical Research, vol. 12, No. 3, 1995, 397-405.

Avella, "Addition of glycerol plasticizer to seaweeds derived alginates: Influences of microstructure on chemical-physical properties," Carbohydrate Polymers vol. 69, Issue 3, Jun. 25, 2007, 503-511.

Babayan, V K. "Preparation and Properties of Some Polyglycerol Esters of Short and Medium Length Fatty Acids," Journal of the American Oil Chemists' Society Jul. 1971, 307-309.

Babayan, V K. et al., "Nutritional Studies of Polyglycerol Esters," the Journal of the American Oil Chemist' Society vol. 41, Jun. 1964, 434-438.

Birnbaum, Duane T. et al., "Microparticle Drug Delivery Systems," Chapter 6, Drug Delivery Systems in Cancer Therapy, 2003, (pp. 117-135).

Bodansky, M et al., "Utilization of Polyglycerol Esters," Biochemistry vol. 32 Aug. 30, 1938, 1938-1942.

Charlemagne, D et al., "Enzymatic Synthesis of Polyglycerol-Fatty Acid Esters in a Solvent-Free System," Journal for American Oil Chemists' Society vol. 72. No. 1 (1995), 61-65.

"Communication Pursuant to Article 94(3) EPC," for European Application No. 10716714, dated Feb. 13, 2015 (6 pages).

"Communication Pursuant to Article 94(3) EPC," for European Application No. 10716714, dated Jan. 18, 2013 (5 pages).

"Communication Pursuant to Article 94(3) EPC," for European Application No. 13792207.6, dated Sep. 29, 2017 (5 pages).

"Communication Pursuant to Article 94(3) EPC," for European Patent Application No. 12723063.9, dated Jun. 12, 2017 (5 pages).

(56) References Cited

OTHER PUBLICATIONS

"Communication Pursuant to Article 94(3) EPC," for European Patent Application No. 14730381.2, dated Nov. 21, 2017 (4 pages).
"Communication Pursuant to Rules 161(1) and 162 EPC," for European Application No. 13792207.6, dated Aug. 5, 2015 (2 pages).
"Communication Pursuant to Rules 161(1) and 162 EPC," for European Patent Application No. 12723063.9, dated Jan. 21, 2014 (2 pages).
"Communication Pursuant to Rules 161(1) and 162 EPC," for European Patent Application No. 14730381.2, dated Jan. 15, 2016 (2 pages).
"Communication Pursuant to Rules 161(1) and 162 EPC," for European Patent Application No. 16703247.3 dated Sep. 15, 2017 (2 pages).
De Meulenaer, B et al., "Development of Chromatographic Method for the Determination of Degree of Polymerisation of Polyglycerols and Polyglycerol Fatty Acid Esters," Chromatographia vol. 51, No. 1/2, Jan. 2000, 44-52.
"Decision of Refusal," for Japanese Patent Application No. 2012-508637, dated Feb. 3, 2015 (3 pages) with English summary.
Dobson, Kevin S. et al., "The Preparation of Polyglycerol Esters Suitable as Low-Caloric Fat Substitutes," Journal of the American Oil Chemists' Society vol. 70, No. 11 (Nov. 1993), 1089-1092.
Dow Corning Corp., "A guide to Silane Solutions," 2005 (30 pages).
FAO Nutrition Meetings Report, "Toxicological Evaluation of Some Antimicrobials, Antioxidants, Emulsifiers, Stabilizers, Flour-treatment Agents, Acids and Bases," FAO Nutrition Meetings Report Series No. 40A, B, C WHO/ Food Add. 67.29 1966, 1-4.
"File History," for U.S. Appl. No. 12/769,127.
"File History," for U.S. Appl. No. 13/469,844.
"File History," for U.S. Appl. No. 13/793,390.
"File History," for U.S. Appl. No. 14/072,520.
"File History," for U.S. Appl. No. 14/280,170.
"File History," for U.S. Appl. No. 14/609,270.
"File History," for U.S. Appl. No. 15/357,496.
"File History," for U.S. Appl. No. 15/385,112.
Finkel, Toren "Relief with Rapamycin: mTOR Inhibition Protects Against Radiation-Induced Mucositis," Cell Stem Cell, vol. 11:3, Sep. 7, 2012 (pp. 1-4).
"First Office Action," for Chinese Application No. 201080018767.7 dated Jun. 8, 2013 (9 pages).
"First Office Action," for Chinese Patent Application No. 2012800328049, dated Mar. 2, 2015 (12 pages) including English translation.
"First Office Action," for Chinese Patent Application No. 201510411761.0 dated Jun. 30, 2017 (13 pages) with English translation.
"Fourth Office Action," for Chinese Patent Application No. 2012800328049, dated May 3, 2017 (8 pages) with English translation.
From Wikipedia, "Electrospinning," From Wikipedia, the free encyclopedia, http://en.wikipedia.org/wiki/Electrospinning, downloaded Sep. 13, 2010; last updated Sep. 2, 2010, 2009, (pp. 1-6).
Ghonaim, Hassan M. et al., "N1,N12-Diacyl Spermines: SAR Studies on Non-viral Lipopolyamine Vectors for Plasmid DNA and siRNA Formulation," Pharmaceutical Research, vol. 27, No. 1, Jan. 2010 (p. 17-29).
Hagemeier, C J. "Ocular Tolerability of Poly(lactide-co-glyoliide) Microspheres Following Subconjunctival and Inravitreal Injection in Rabbit Eyes," ARVO 2010 Presented ARVO 2010, Hall B/C, May 6, 2010 8:30am-10:15am May 6, 2010.
Howes, D et al., "The Fate of Ingested Glyceran Esters of Condensed Castor Oil Fatty Acids [Polyglycerol Polyricinoleate (PGPR)] in the Rat," Food and Chemical Toxicology 36 (1998) pp. 719-738.
"International Preliminary Report on Patentability," for PCT Application No. PCT/US2016/015644 dated Aug. 10, 2017 (12 pages).
"International Preliminary Report on Patentability," for PCT/US2012/038158, dated Nov. 28, 2013 (8 pages).
"International Preliminary Report on Patentability," for PCT/US2013/068539, dated May 14, 2015 (9 pages).
"International Preliminary Report on Patentability," for PCT/US2014/038435 dated Nov. 26, 2015 (10 pages).
"International Search Report & Written Opinion," for PCT/US2016/015644 dated Jul. 11, 2016 (17 pages).
"International Search Report and Written Opinion," for PCT/US2010/032741 dated Dec. 13, 2010 (11 pages). Dec. 13, 2010, 11 pages.
"International Search Report and Written Opinion," for PCT/US2012/038158, dated Sep. 27, 2012 (13 pages).
"International Search Report and Written Opinion," for PCT/US2013/068539, dated Jan. 22, 2014 (12 pages).
"International Search Report and Written Opinion," for PCT/US2014/038435, dated Aug. 25, 2014 (13 pages).
"Invitation to Pay Additional Fees and Partial Search Report," for PCT Application No. PCT/US2016/015644, dated May 3, 2016 (8 pages).
"Invitation to Respond to Written Opinion," for SG Patent Application No. 201107896-1, dated Jun. 12, 2012 (6 pages).
Kallinteri, Paraskevi et al., "Novel Functionalized Biodegradable Polymers for Nanoparticle Drug Delivery Systems," Biomacromolecules 2005 2006, 6, 1885-1894; American Chemical Society Apr. 27, 2005.
Kumar, Majeti N.V. R. "Nano and Microparticles as Controlled Drug Delivery Devices," J. Pharm Pharmaceut Sci, 3(2), 2000 (pp. 234-258).
Liu, Rong "Water-Insoluble Drug Formulation," CRC Press, 2nd Ed., 2008 (pp. 1-3).
Love, Kevin T. et al., "Lipid-Like Materials for Low-Dose in Vivo Gene Silencing," PNAS Feb. 2010, 107 (5) 1864-1869, www.pnas.org/cgi/doi/10.1073/pnas.0910603106 (6 pages).
McIntyre, R T. "Polyglycerol esters," Journal of American Oil Chemists' Society Nov. 1979 (vol. 56) Nov. 1979, 835A-840A.
Mugabe, Clement et al., "Paclitaxel Incorporated in Hydrophobically Derived Hyperbranched Polyglycerols for Intravesical Bladder Cancer Therapy," BJU International, 2008, vol. 103, p. 978-986.
"Non-Final Office Action," for Japanese Patent Application No. 2012-508637, dated Mar. 18, 2014 (4 pages) with English translation.
"Non-Final Office Action," for Mexican Patent Application No. MX/a/2011/011389, dated Aug. 18, 2015 (1 page).
"Non-Final Office Action," for Mexican Patent Application No. MX/a/2011/011389, dated Feb. 22, 2016 (1 page).
"Non-Final Office Action," for U.S. Appl. No. 15/850,010 dated Jan. 24, 2018 (7 pages).
"Notification for Patent Reexamination," for Chinese Patent Application No. 201080018767.7, dated Sep. 25, 2014 (12 pages) with English translation.
"Office Action," for Canadian Patent Application No. 2,760,187 dated Jan. 12, 2017 (3 pages).
"Office Action," for Canadian Patent Application No. 2,760,187 dated Mar. 24, 2016 (4 pages).
"Office Action," for Japanese Patent Application No. 2014511494 dated Feb. 5, 2016 (13 pages) with English Translation.
"Office Action," for Japanese Patent Application No. 2014511494 dated Nov. 25, 2016 (6 pages) with English Translation.
"Office Action," for Japanese Patent Application No. 2015-540868 dated Aug. 31, 2017 (10 pages) with English translation.
Orafei, Hossein et al., "Novel Poly(glycerol-adipate) Polymers Used for Nanoparticle Making: A Study of Surface Free Energy," Iranian Journal of Pharmaceutical Research (2008), 7 (1): 11-19.
"PCT Notification Concerning Transmittal of International Preliminary Report on Patentability," from International Application No. PCT/US10/032741, dated Nov. 10, 2011, pp. 1-8.
Puri, Sanyogita "Drug Incorporation and Release of Water Soluble Drugs from Novel Functionalized Poly(glycerol adipate) Nanoparticles," Journal of Controlled Release 125 (2008) 59-67 Oct. 10, 2007.
Renkin, Eugene M. "Filtration, Diffusion, and Molecular Sieving Through Porous Cellulose Membranes," Nov. 20, 1954 (pp. 1-19).
"Response to Communication Pursuant to Article 94(3) EPC," for European Application No. 10716714.0 filed with EPO Aug. 11, 2015 (51 pages).

(56) References Cited

OTHER PUBLICATIONS

"Response to Communication Pursuant to Article 94(3) EPC," for European Application No. 10716714.0 filed with EPO Jun. 10, 2013 (9 pages).
"Response to Communication Pursuant to Article 94(3) EPC," for European Patent Application No. 12723063.9 filed with the EPO Nov. 16, 2017 (9 pages).
"Response to Communication Pursuant to Article 94(3) EPC," for European Patent Application No. 14730381.2, filed with the European Patent Office Dec. 21, 2017 (68 pages).
"Response to Communication Pursuant to Rule 161 and 162 EPC," for European Patent Application 12723063.9, dated Jan. 21, 2014 and filed with the EPO Jul. 18, 2014 (4 pages).
"Response to Communication Pursuant to Rules 161(1) and 162 EPC," for European Application No. 13792207.6, filed with the EPO Feb. 3, 2016 (4 pages).
"Response to Communication Pursuant to Rules 161(1) and 162 EPC," for European Patent Application No. 14730381.2, filed with the European Patent Office Jul. 14, 2016 (14 pages).
"Response to Office Action," for Canadian Patent Application No. 2,760,187 filed with CIPO Feb. 15, 2017 (5 pages).
"Response to Office Action," for Canadian Patent Application No. 2,760,187 filed with CIPO Sep. 22, 2016 (22 pages).
Salamone, Joseph "Hydrophic Polymers (for Friction Reduction)," Polymeric Materials Encyclopedia, vol. 12 (1996) p. 3107.
Santoyo, Antonio B. et al., "Biosynthesis of Polyglycerol Polyricinoleate (PGPR) with Rhizopus Arrhizus Lipase," Journal of Biotechnology 131S (2007) S74-S97 2007, S82.
Scheller, Bruno et al., "Paclitaxel Balloon Coating, a Novel Method for Prevention and Therapy of Restenosis," Circulation, Journal of the American Heart Association; 2004 (110);810-814. Online version of article: http://circ.ahajournals.org/cgi/content/full/11/7/810, downloaded Jan. 12, 2011 2004, 6 pages.
"Second Office Action," for China Patent Application No. 2012800328049, dated Jan. 26, 2016 (9 pages), with translation.
"Second Office Action," for Chinese Patent Application No. 201510411761.0 dated Dec. 22, 2017 (11 pages) with English translation.
Solvay Chemicals, "Polyglycerols for Ester Production," PGLC-05-002 Revised 8-2008 CGR4004, From www.solvaychemicals.us Aug. 2008, 1-7.
Takatori, Toshihito "Design of Controlled-Release Morphine Suppositories Containing Polyglycerol Ester of Fatty Acid," Biological Phamacy Bulletin 28(8) 1480-1484 (2005).
"Third Office Action," for Chinese Patent Application No. 2012800328049, dated Aug. 11, 2016 (12 pages) with English translation.
Yamagata, Yutaka et al., "Novel Sustained Release Dosage Forms of Proteins Using Polyglycerol Esters of Fatty Acids," Journal of Controlled Release vol. 63, Issue 3 Feb. 3, 2000, 319-329.
"Communication Pursuant to Article 94(3) EPC," for European Patent Application No. 16703247.3 dated Sep. 4, 2018 (5 pages).
"Final Office Action," for U.S. Appl. No. 15/850,010 dated Oct. 2, 2018 (35 pages).
"First Examination Report," for Indian Patent Application No. 3723/KOLNP/2013 dated Sep. 28, 2018 (5 pages).
"International Search Report and Written Opinion," for PCT Application No. PCT/US2017/066573 dated Apr. 3, 2018 (10 pages).
"Non Final Office Action," for U.S. Appl. No. 14/280,170 dated Oct. 5, 2018 (36 pages).
"Non-Final Office Action," for U.S. Appl. No. 13/793,390 dated Jul. 13, 2018 (48 pages).
"Non-Final Office Action," for U.S. Appl. No. 15/385,112 dated Aug. 13, 2018 (8 pages).
"Notice of Allowance," for U.S. Appl. No. 15/385,112 dated Oct. 5, 2018 (10 pages).
"Office Action," for Canadian Patent Application No. 2,836,266 dated Apr. 11, 2018 (3 pages).
"Office Action," for Japanese Patent Application No. 2015-540868 dated May 21, 2018 (6 pages) with English translation.
"Office Action," for Japanese Patent Application No. 2016-514136 dated Apr. 10, 2018 (7 pages) with English translation.
"Office Action," for Mexican Patent Application No. MX/a/2015/015589 dated Sep. 9, 2018 (1 page), translation only.
"Response to Communication Pursuant to Article 94(3) EPC," for European Patent Application No. 13792207.6, filed with the EPO Mar. 29, 2018 (25 pages).
"Response to Communication Pursuant to Rules 161(1) and 162 EPC," for European Patent No. 16703247.3 filed with the EPO on Mar. 22, 2018.
"Response to Final Office Action," for U.S. Appl. No. 13/793,390, dated Jan. 11, 2018 and filed with the USPTO Jun. 11, 2018 (17 pages).
"Response to Non-Final Office Action," for U.S. Appl. No. 15/385,112, filed with the USPTO Apr. 20, 2018 (15 pages) for Non-Final Office Action dated Jan. 11, 2018.
"Response to Non-Final Office Action," for U.S. Appl. No. 15/850,010, dated Jan. 24, 2018 and filed with the USPTO Jun. 11, 2018 (8 pages).
"Response to Non-Final Rejected," dated Aug. 13, 2018, for U.S. Appl. No. 15/385,112, submitted via EFS-Web on Sep. 12, 2018, 5 pages.
"Response to Non-Final Rejection," dated Jul. 13, 2018, for U.S. Appl. No. 13/793,390, submitted via EFS-Web on Sep. 12, 2018, 6 pages.
"Response to Office Action," for Canadian Patent Application No. 2,836,266 filed with CIPO Sep. 20, 2018 (28 pages).
"Third Office Action," for Chinese Patent Application No. 201510411761.0 dated Jul. 25, 2018 (14 pages) with English translation.
"Notice of Allowance," for U.S. Appl. No. 13/793,390 dated Oct. 31, 2018 (10 pages).
"Office Action," for Canadian Patent Application No. 2,836,266 dated Nov. 30, 2018 (4 pages).
"Response to Non-Final Office Action," for U.S. Appl. No. 14/280,170 filed with the USPTO Dec. 10, 2018 (18 pages).
"Communication Pursuant to Article 94(3) EPC," for European Patent Application No. 12723063.9 dated Jan. 16, 2019 (5 pages).
"Communication Pursuant to Article 94(3) EPC," for European Patent Application No. 16703247.3 dated Apr. 23, 2019 (5 pages).
"Decision of Rejection," for Chinese Patent Application No. 201510411761.0 dated Nov. 30, 2018 (19 pages) with English Translation.
"Final Office Action," for U.S. Appl. No. 14/280,170 dated Apr. 5, 2019 (38 pages).
"Non-Final Office Action," for U.S. Appl. No. 15/850,010 dated Feb. 26, 2019 (13 pages).
"Response to Communication Pursuant to Article 94(3) EPC," for European Patent Application No. 16703247.3 filed Dec. 20, 2018 (7 pages).
"Response to Final Office Action," for U.S. Appl. No. 15/850,010 filed with the USPTO Jan. 24, 2019 (10 pages).
"Response to First Examination Report," for Indian Patent Application No. 3723/KOLNP/2013 filed Feb. 20, 2019 (23 pages).
"First Office Action," for Russian Patent Application No. 2017129933 dated Jun. 27, 2019 (10 pages) with English Translation.
"International Preliminary Report on Patentability," for PCT Application No. PCT/US2017/066573 dated Jul. 4, 2019 (7 pages).
"Non-Final Office Action," for U.S. Appl. No. 15/994,263 dated Aug. 14, 2019 (50 pages).
"Notice of Allowance," for U.S. Appl. No. 15/850,010 dated Oct. 23, 2019 (14 pages).
"Office Action Response," for Israeli Patent Application No. 242545 filed Sep. 28, 2019 (133 pages) English Translation.
"Office Action," for Canadian Patent Application No. 2,836,266 dated Oct. 23, 2019 (3 pages).
"Office Action," for Canadian Patent Application No. 2,890,205 dated Sep. 18, 2019 (5 pages).
"Office Action," for Israeli Patent Application No. 242545 dated May 28, 2019 (8 pages) with English Translation.
"Preliminary Office Action," for Brazilian Patent Application No. 1120170136420 dated Oct. 15, 2019 (7 pages) with English Translation.

(56) References Cited

OTHER PUBLICATIONS

"Response to communication Pursuant to Article 94(3) EPC," for European Patent Application No. 12723063.9 filed Jul. 2, 2019 (56 pages).

"Response to Communication Pursuant to Article 94(3) EPC," for European Patent Application No. 16703247.3 filed Aug. 30, 2019 (10 pages).

"Response to Final Rejection," dated Apr. 5, 2019 for U.S. Appl. No. 14/280,170, submitted via EFS-Web on Aug. 2, 2019, 12 pages.

"Response to Non-Final Office Action," for U.S. Appl. No. 15/944,253 filed with the USPTO Nov. 12, 2019 (15 pages).

"Response to Non-Final Rejection," dated Feb. 26, 2019 for U.S. Appl. No. 15/850,010, submitted via EFS-Web on Jun. 26, 2019, 6 pages.

"Response to Office Action," for Canadian Patent Application No. 2,836,266 filed May 29, 2019 (19 pages).

Chen, Xia-Chao et al., "Humidity-Triggered Self-Healing of Microporous Polyelectrolyte Multilayer Coatings for Hydrophobic Drug Delivery," Advanced Functional Materials, vol. 25, No. 48, Dec. 1, 2015 pp. 7470-7477 (8 pages).

"Communication Pursuant to Article 94(3) EPC," for European Patent Application No. 16703247.3 dated Feb. 12, 2020 (7 pages).

"Final Office Action," for U.S. Appl. No. 15/994,263 dated Jan. 16, 2020 (29 pages).

"First Examination Report," for Indian Patent Application No. 201747029823 dated Nov. 25, 2019 (6 pages).

"First Office Action," for Chinese Patent Application No. 2016800187265 dated Nov. 5, 2019 (9 pages) with English Translation.

"Office Action," for Israeli Patent Application No. 242545 dated Feb. 6, 2020 (7 pages) with English Translation.

"Office Action," for Japanese Patent Application No. 2017-540169 dated Nov. 21, 2019 (12 pages) with English Translation.

"Office Action," for Russian Patent Application No. 2017129933 dated Oct. 21, 2019 (9 pages) with English Translation.

"Response to Communication Pursuant to Rules 161(1) and 162 EPC," for European Patent Application No. 17835893.3 filed Jan. 21, 2020 (7 pages).

"Written Submissions in Respect of Hearing on Nov. 14, 2019," for Indian Patent Application No. 3723/KOLNP/2013 filed Nov. 23, 2019 (19 pages).

"Communication Pursuant to Article 94(3) EPC," for European Patent Application No. 17835893.3 dated Jun. 29, 2020 (5 pages).

"Non-Final Office Action," for U.S. Appl. No. 14/280,170 dated Apr. 15, 2020 (32 pages).

"Non-Final Office Action," for U.S. Appl. No. 15/994,263 dated Jul. 15, 2020 (24 pages).

"Office Action," for Canadian Patent Application No. 2,912,690 dated Apr. 29, 2020 (5 pages).

"Office Action," for Russian Patent Application No. 2017129933 dated Mar. 2, 2020 (9 pages) with English Translation.

"Reexamination Notification," for Chinese Patent Application No. 201510411761.0 dated Jun. 3, 2020 (13 pages) with English Translation.

"Response to Final Office Action," for U.S. Appl. No. 15/994,263 filed Apr. 16, 2020 (8 pages).

"Response to First Examination Report," for Indian Patent Application No. 201747029823 filed May 22, 2020 (13 pages).

"Response to Non-Final Office Action," for U.S. Appl. No. 14/280,170 filed with the USPTO Jul. 14, 2020 (11 pages).

"Response to Office Action," for Canadian Patent Application No. 2,836,266 filed Apr. 15, 2020 (18 pages).

"Response to Office Action," for Canadian Patent Application No. 2,890,205 filed Mar. 18, 2020 (28 pages).

"Response to Office Action," for Israeli Patent Application No. 242545 filed Jun. 7, 2020 (15 pages).

"Second Office Action," for Chinese Patent Application No. 2016800187265 dated Jun. 10, 2020 (10 pages) with English Translation.

\* cited by examiner

US 10,898,446 B2

DELIVERY OF HYDROPHOBIC ACTIVE AGENTS FROM HYDROPHILIC POLYETHER BLOCK AMIDE COPOLYMER SURFACES

This application claims the benefit of U.S. Provisional Application No. 62/436,694, filed Dec. 20, 2016, the contents of which are herein incorporated by reference.

FIELD OF THE INVENTION

The present invention relates to devices and coatings for medical device. More specifically, the present invention relates to devices and coatings for medical devices including hydrophilic polyether block amide copolymer and hydrophobic active agent particles disposed thereon.

BACKGROUND OF THE INVENTION

The vascular system of the human is subject to blockage due to plaque within the arteries. Partial and even complete blockage of arteries by the formation of an atherosclerotic plaque is a well-known and frequent medical problem. Frequently, such blockage occurs in the coronary arteries. Blockages may also occur secondary to past treatment of specific sites (restenosis—such as that stemming from rapidly dividing smooth muscle cells). In addition, blockages can also occur in the context of peripheral arteries.

Blockages may be treated using atherectomy devices, which mechanically remove the plaque; hot or cold lasers, which vaporize the plaque; stents, which hold the artery open; and other devices and procedures designed to increase blood flow through the artery.

One common procedure for the treatment of blocked arteries is percutaneous transluminal coronary angioplasty (PTCA), also referred to as balloon angioplasty. In this procedure, a catheter having an inflatable balloon at its distal end is introduced into the coronary artery, the deflated, folded balloon is positioned at the stenotic site, and then the balloon is inflated. Inflation of the balloon disrupts and flattens the plaque against the arterial wall, and stretches the arterial wall, resulting in enlargement of the intraluminal passageway and increased blood flow. After such expansion, the balloon is deflated, and the balloon catheter removed. A similar procedure, called percutaneous transluminal angioplasty (PTA), is used in arteries other than coronary arteries in the vascular system. In other related procedures, a small mesh tube, referred to as a stent is implanted at the stenotic site to help maintain patency of the coronary artery. In rotoblation procedures, also called percutaneous translumininal rotational atherectomy (PCRA), a small, diamond-tipped, drill-like device is inserted into the affected artery by a catheterization procedure to remove fatty deposits or plaque. In a cutting balloon procedure, a balloon catheter with small blades is inflated to position the blades, score the plaque and compress the fatty matter into the artery wall. During one or more of these procedures, it may be desirable to deliver a therapeutic agent or drug to the area where the treatment is occurring to prevent restenosis, repair vessel dissections or small aneurysms or provide other desired therapy.

Additionally, it may be desirable to transfer therapeutic agents to other locations in a mammal, such as the skin, neurovasculature, nasal, oral, the lungs, the mucosa, sinus, the GI tract or the renal peripheral vasculature.

SUMMARY OF THE INVENTION

Embodiments of the invention include drug delivery coatings and devices including the same. In an embodiment a drug delivery coating is included. The drug delivery coatings including a base polymeric layer, the base polymeric layer including a hydrophilic polyether block amide copolymer and having a hydrophilic surface. The drug delivery coating can further include a therapeutic agent layer forming an exterior surface the drug delivery coating, the therapeutic agent layer contacting the hydrophilic surface of the base polymeric layer and having a composition different than the base polymeric layer. The therapeutic agent layer can include a particulate hydrophobic therapeutic agent and a cationic agent.

In an embodiment a drug delivery device is included. The drug delivery device can include a substrate comprising a hydrophilic polyether block amide copolymer and having a hydrophilic surface. The drug delivery device can further include a therapeutic agent layer forming an exterior surface of at least a portion of the drug delivery device, the therapeutic agent layer contacting the hydrophilic surface of the substrate. The therapeutic agent layer can include a particulate hydrophobic therapeutic agent and a cationic agent.

In an embodiment, a method of making a medical device is included. The method can include depositing a therapeutic agent layer onto at least a portion of the medical device, the medical device comprising a substrate comprising a hydrophilic polyether block amide copolymer. The therapeutic agent layer can be contacting the surface of the substrate. The therapeutic agent layer can include a particulate hydrophobic therapeutic agent and a cationic agent.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

Figure 1:
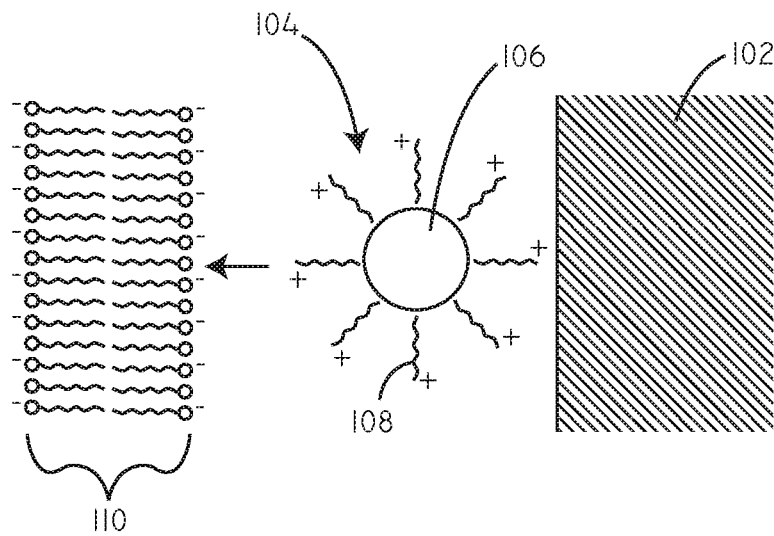
FIG. 1 is a schematic cross-sectional diagram of a coating in accordance with an embodiment herein.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As described above, in association with procedures such as percutaneous transluminal coronary angioplasty (PTCA), percutaneous transluminal angioplasty (PTA), and the like, it can be desirable to deliver a therapeutic agent or drug to the area where the treatment is occurring to prevent restenosis, repair vessel dissections or small aneurysms or provide other desired therapy. One approach for accomplishing this is to deliver a therapeutic agent (or active agent) to the desired tissue site using a drug delivery device such as a drug eluting balloon catheter or a drug-containing balloon catheter.

Drug delivery coatings for certain medical applications desirably exhibit various properties. By way of example, in the context of a drug eluting balloon catheter or a drug-containing balloon catheter, the coating should maintain structural integrity during steps associated with preparation of the balloon catheter device include pleating, folding, and curing (such as heat treatment). In addition, it is desirable for the coating to maintain structural integrity during the process of passing through the vasculature through a catheter and/or over the guide wire, with limited loss of the active agent. Yet, it is also desirable upon inflation of the balloon at the desired site to transfer a substantial amount of the active agent from the balloon and onto the vessel wall. In addition, it is desirable to maximize uptake of the active agent into the tissue of the of the vessel wall and reduce the amount of active agent that is washed away into the blood flowing through the treatment site in the vasculature.

Embodiments herein can be useful to enhance one or more desirable properties of drug delivery coatings, such as those properties desirable in the context of drug eluting balloon catheters, drug-containing balloon catheters and similar devices. In various embodiments, a drug delivery device is provided that includes a substrate and coated therapeutic agent particles disposed on the substrate. The coated therapeutic agent particles can include a particulate hydrophobic therapeutic agent and a cationic agent disposed over the particulate hydrophobic therapeutic agent.

Referring now to FIG. 1, a schematic cross-sectional diagram (not to scale) is provided of a coating in accordance with an embodiment herein. In this embodiment, coated therapeutic agent particles 104 are disposed on a substrate 102. Exemplary substrates are described in greater detail below. The coated therapeutic agent particles 104 can include a plurality of cationic agents 108 disposed over a particulate hydrophobic therapeutic agent 106. The coated therapeutic agent particles 104 can be contiguously coated with cationic agents 108. In other embodiments, the cationic agent 108 coating on the therapeutic agent particles 104 can be discontinuous. Additionally, the particulate hydrophobic agents 106 can coexist in a matrix with cationic agents 108 wherein the cationic agent 108 does not coat the particulate hydrophobic agent 106. Various mixtures of the embodiments described above can be found on a specific substrate 102. For example, but not limiting, a coating on a substrate can include coated therapeutic agent particles 104 contiguously coated with cationic agents 108 and particulate hydrophobic agents 106 in a matrix with cationic agents 108 wherein the cationic agent 108 does not coat the particulate hydrophobic agent 106. It will be appreciated that as actually applied there will be many hydrophobic therapeutic agent particulates within a given coating and that a single particulate is shown in FIG. 1 just for purposes of ease of illustration. Exemplary cationic agents and hydrophobic therapeutic agents are described in greater detail below. The charge provided by the cationic agents 108 can be electrostatically attracted to negative charges and/or polar groups associated with the lipid bilayer 110 of a cell membrane and cellular components within the lipid bilayer 110.

Figure 2:
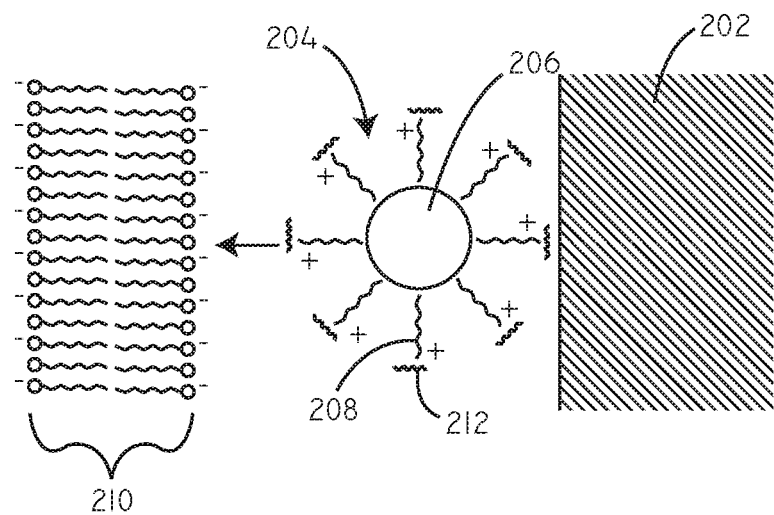
FIG. 2 is a schematic cross-sectional diagram of a coating in accordance with an embodiment herein.

In some embodiments, nucleic acids may also be included in coatings herein. By way of example, nucleic acids, including but not limited to siRNA, may be associated with the cationic agent. Exemplary nucleic acids are described in greater detail below. Referring now to FIG. 2, a schematic cross-sectional diagram (not to scale) is provided of another embodiment herein. In this embodiment, coated therapeutic agent particles 204 are disposed on a substrate 202. The coated therapeutic agent particles 204 can include a plurality of cationic agents 208 disposed over a particulate hydrophobic therapeutic agent 206. Nucleic acids 212 can be associated with the cationic agent. The charge provided by the cationic agents 208 can be electrostatically attracted to negative charges and/or polar groups associated with the lipid bilayer 210 of a cell membrane and cellular components within the lipid bilayer 210.

Figure 3:
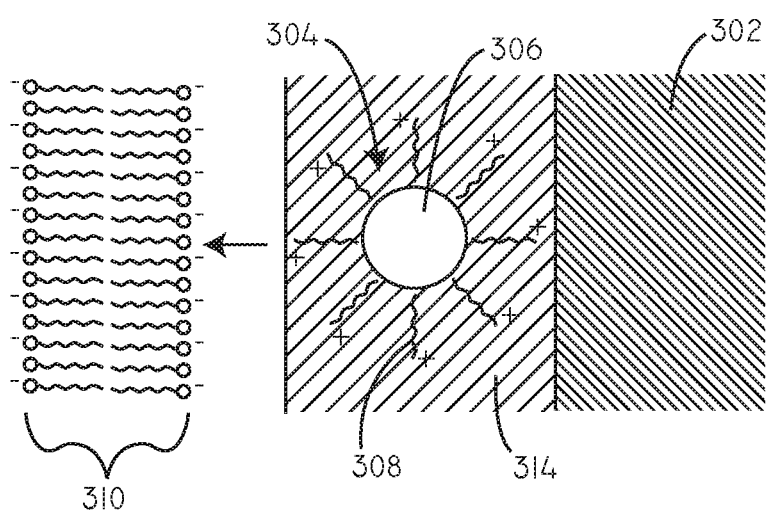
FIG. 3 is a schematic cross-sectional diagram of a coating in accordance with an embodiment herein.

In some embodiments, an additive may be included along with the coated therapeutic agent particles 304 in coatings herein. Referring now to FIG. 3, a schematic cross-sectional diagram (not to scale) is provided of another embodiment. In this embodiment, coated therapeutic agent particles 304 are disposed on a substrate 302. An additive 314 can be disposed along with the coated therapeutic agent particles 304. The amount of the additive 314 can be more than, less than, or equal to the amount of the coated therapeutic agent particles 304. In some embodiments, the additive 314 can form a matrix or layer in which the coated therapeutic agent particles 304 are disposed. In various embodiments, the additive can be hydrophilic. Exemplary additive components are described in greater detail below. The coated therapeutic agent particles 304 can include a plurality of cationic agents 308 disposed over a particulate hydrophobic therapeutic agent 306. The charge provided by the cationic agents 308 can be electrostatically attracted to negative charges and/or polar groups associated with the lipid bilayer 310 of a cell membrane and cellular components within the lipid bilayer 310.

Figure 4:
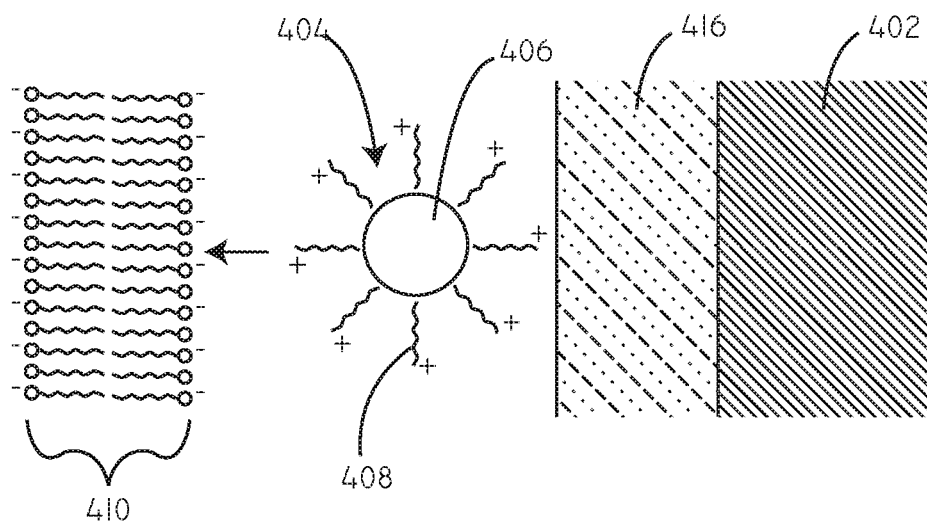
FIG. 4 is a schematic cross-sectional diagram of a coating in accordance with an embodiment herein.

In some embodiments, a hydrophilic polymer layer can be disposed on the surface of the substrate, between the coated therapeutic agent particles and the surface of the substrate. Exemplary polymers for the hydrophilic polymer layer are described in greater detail below. Referring now to FIG. 4, a schematic cross-sectional diagram (not to scale) is provided of another embodiment herein. In this embodiment, coated therapeutic agent particles 404 are disposed on a hydrophilic polymer layer 416, which is in turn disposed on a substrate 402. The coated therapeutic agent particles 404 can include a plurality of cationic agents 408 disposed over a particulate hydrophobic therapeutic agent 406. The charge provided by the cationic agents 408 can be electrostatically attracted to negative charges and/or polar groups associated with the lipid bilayer 410 of a cell membrane and cellular components within the lipid bilayer 410.

Figure 5:
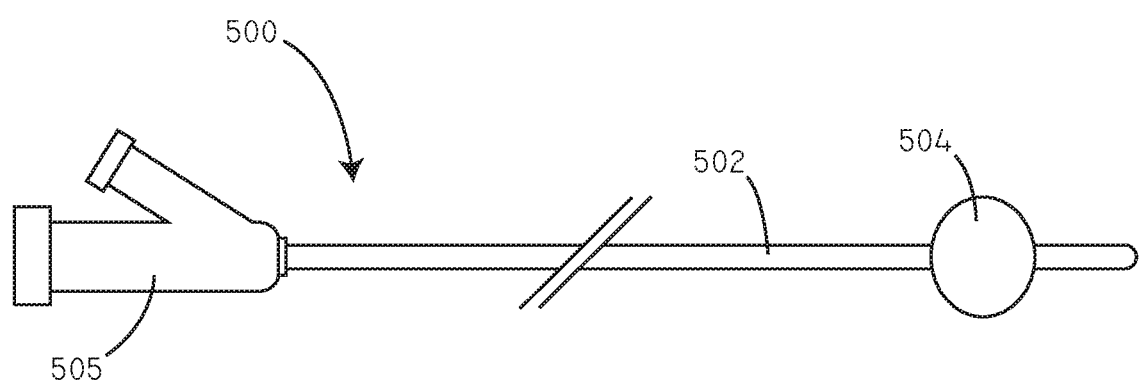
FIG. 5 is a schematic diagram of a device in accordance with an embodiment herein.

Referring now to FIG. 5, a schematic view of an exemplary device is shown in accordance with an embodiment. The device 500 can be, for example, an angioplasty balloon catheter or a drug eluting balloon catheter or a drug-containing balloon catheter. However, further examples of exemplary devices are described in greater detail below. The device 500 includes a catheter shaft 502 and a manifold end 505. The device 500 also includes an inflatable balloon 504 disposed around the catheter shaft 502. In FIG. 5, the balloon 504 is shown in an inflated configuration. The catheter shaft 502 can include a channel to convey fluid through the catheter shaft 502 and to or from the balloon 504, so that the balloon 504 can selectively go from a deflated configuration to the inflated configuration and back again.

The manufacture of expandable balloons is well known in the art, and any suitable process can be carried out to provide the expandable substrate portion of the insertable medical device as described herein. Catheter balloon construction is described in various references, for example, U.S. Pat. Nos. 4,490,421, 5,556,383, 6,210,364, 6,168,748, 6,328,710, and 6,482,348. Molding processes are typically performed for balloon construction. In an exemplary molding process, an extruded polymeric tube is radially and axially expanded at elevated temperatures within a mold having the desired shape of the balloon. The balloon can be subjected to additional treatments following the molding process. For example, the formed balloon can be subjected to additional heating steps to reduce shrinkage of the balloon.

Referring back to FIG. 5, the insertable medical device 500 can also have one or more non-expandable (or inelastic) portions. For example, in a balloon catheter, the catheter shaft 502 portion can be the non-expandable portion. The non-expandable portion can be partially or entirely fabricated from a polymer. Polymers include those formed of synthetic polymers, including oligomers, homopolymers, and copolymers resulting from either addition or condensation polymerizations.

Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, polyamides such as poly-caprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone. The non-expandable portion can also be partially or entirely fabricated from a metal.

Figure 6:
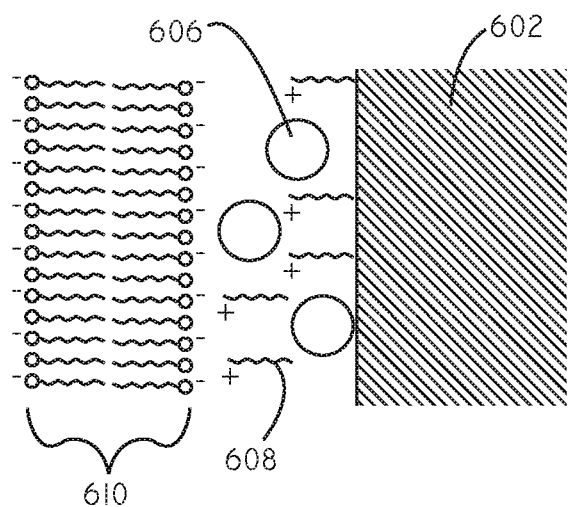
FIG. 6 is a schematic cross-sectional diagram of a coating in accordance with various embodiments herein.

Referring now to FIG. 6, a schematic cross-sectional diagram (not to scale) is provided of a drug delivery coating in accordance with various embodiments herein. In this embodiment, particulate hydrophobic therapeutic agents 606 are disposed on a substrate 602. Exemplary substrates are described in greater detail below. A plurality of cationic agents 608 are also disposed on the substrate. The particulate hydrophobic therapeutic agents 606 and the cationic agents 608 can form a matrix. It will be appreciated that as actually applied there can be many more hydrophobic therapeutic agent particulates within a given matrix. Exemplary cationic agents and hydrophobic therapeutic agents are described in greater detail below. The charge provided by the cationic agents 608 can be electrostatically attracted to negative charges and/or polar groups associated with the lipid bilayer 610 of a cell membrane and cellular components within the lipid bilayer 610.

Figure 7:
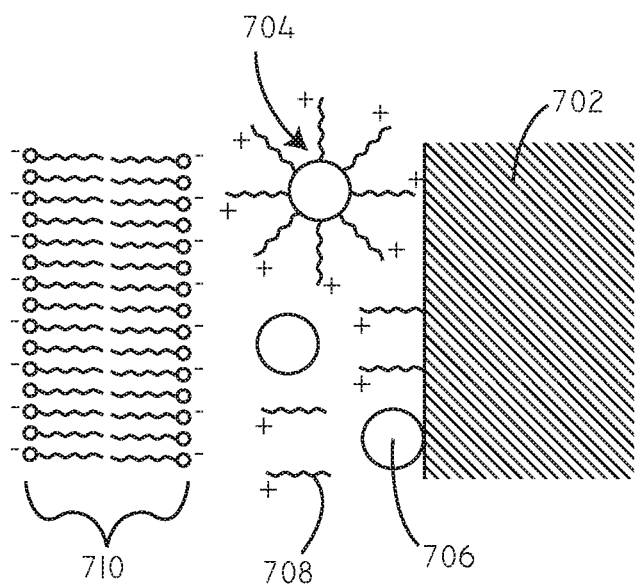
FIG. 7 is a schematic cross-sectional diagram of a coating in accordance with various embodiments herein.

Referring now to FIG. 7, a schematic cross-sectional diagram (not to scale) is provided of a drug delivery coating in accordance with various embodiments herein. In this embodiment, particulate hydrophobic therapeutic agents 706 are disposed on a substrate 702. A plurality of cationic agents 708 are also disposed on the substrate. The particulate hydrophobic therapeutic agents 706 and the cationic agents 708 can form a matrix. The particulate hydrophobic therapeutic agents 706 and the cationic agents 708 can be associated with one another and in some cases can form coated therapeutic agent particles 704 disposed on the substrate 702. The coated therapeutic agent particles 704 can include a plurality of cationic agents 708 disposed over a particulate hydrophobic therapeutic agent 706. It will be appreciated that as actually applied there can be many hydrophobic therapeutic agent particulates within a given coating and that particulates shown in FIG. 7 are just for purposes of ease of illustration. The charge provided by the cationic agents 708 can be electrostatically attracted to negative charges and/or polar groups associated with the lipid bilayer 710 of a cell membrane and cellular components within the lipid bilayer 710.

Figure 8:
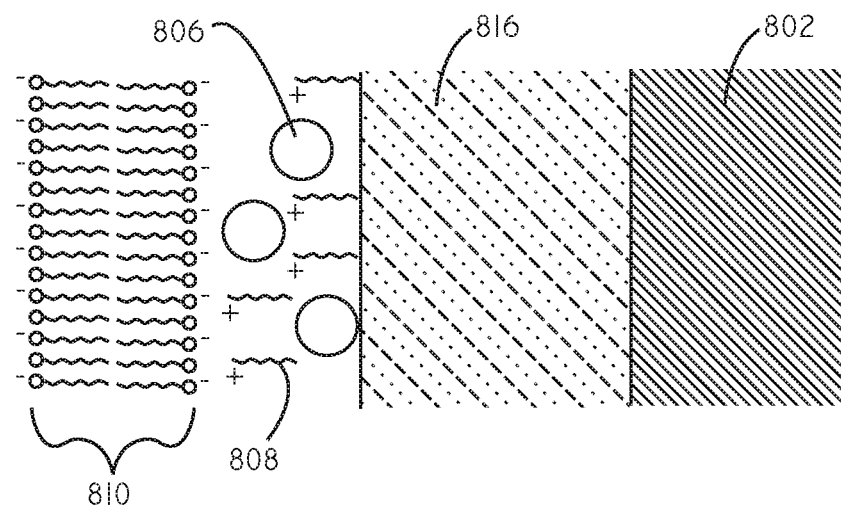
FIG. 8 is a schematic cross-sectional diagram of a coating in accordance with various embodiments herein.

In some embodiments, a hydrophilic polymer layer can be disposed on the surface of the substrate, between the therapeutic agent, cationic agent, and/or coated therapeutic agent particles and the surface of the substrate. Exemplary polymers for the hydrophilic polymer layer are described in greater detail below. Referring now to FIG. 8, a schematic cross-sectional diagram (not to scale) is provided of a drug delivery coating in accordance with various embodiments herein. A hydrophilic polymer layer 816 is disposed on a substrate 802. Particulate hydrophobic therapeutic agents 806 are disposed on the hydrophilic polymer layer 816. A plurality of cationic agents 808 can also be disposed on the hydrophilic polymer layer 816. The particulate hydrophobic therapeutic agents 806 and the cationic agents 808 can be associated with one another. The particulate hydrophobic therapeutic agents 806 and the cationic agents 808 can form a matrix. The charge provided by the cationic agents 808 can be electrostatically attracted to negative charges and/or polar groups associated with the lipid bilayer 810 of a cell membrane and cellular components within the lipid bilayer 810.

Figure 9:
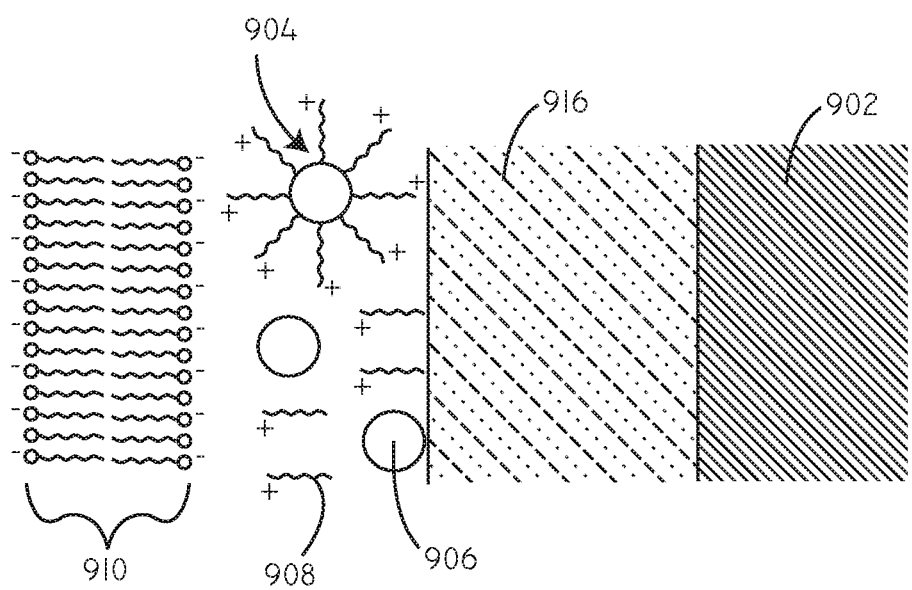
FIG. 9 is a schematic cross-sectional diagram of a coating in accordance with various embodiments herein.

Referring now to FIG. 9, a schematic cross-sectional diagram (not to scale) is provided of a drug delivery coating in accordance with various embodiments herein. A hydrophilic polymer layer 916 is disposed on a substrate 902. Particulate hydrophobic therapeutic agents 906 can be disposed on the hydrophilic polymer layer 916. A plurality of cationic agents 908 can also disposed on the hydrophilic polymer layer 916. The particulate hydrophobic therapeutic agents 906 and the cationic agents 908 can form a matrix. The particulate hydrophobic therapeutic agents 906 and the cationic agents 908 can be associated with one another and in some cases can form coated therapeutic agent particles 904 disposed on the hydrophilic polymer layer 916. The coated therapeutic agent particles 904 can include a plurality of cationic agents 908 disposed over a particulate hydrophobic therapeutic agent 906. The charge provided by the cationic agents 908 can be electrostatically attracted to negative charges and/or polar groups associated with the lipid bilayer 910 of a cell membrane and cellular components within the lipid bilayer 910.

Cationic Agents

Cationic agents used in embodiments herein can include compounds containing a portion having a positive charge in aqueous solution at neutral pH along with a portion that can exhibit affinity for hydrophobic surfaces (such as hydrophobic or amphiphilic properties) and can therefore interface with hydrophobic active agents. In some embodiments, cationic agents used in embodiments herein can include those having the general formula X-Y, wherein X is a radical including a positively charged group in aqueous solution at neutral pH and Y is a radical exhibiting hydrophobic properties. In some embodiments, the cationic agent can include a hydrophilic head and a hydrophobic tail, along with one or more positively charged groups, typically in the area of the hydrophilic head.

Cationic agents of the present disclosure can include salts of cationic agents at various pH ranges, such as, but not limited to, halide salts, sulfate salts, carbonate salts, nitrate salts, phosphate salts, acetate salts and mixtures thereof.

Cationic agents can specifically include cationic lipids and net neutral lipids that have a cationic group (neutral lipids with cationic groups). Exemplary lipids can include, but are not limited to, 3β[N—(N',N'-dimethylaminoethane)-carbamoyl]cholesterol hydrochloride (DC-cholesterol); 1,2-dioleoyl-3-trimethylammonium-propane (DOTAP); dimethyldioctadecylammonium (DDAB); 1,2-dioleoyl-sn-glycero-3-ethylphosphocholine (EPC); 1,2-di-O-octadecenyl-3-trimethylammonium propane (DOTMA); 1,2-di-(9Z-octadecenoyl)-3-dimethylammonium-propane (DODAP); 1,2-dilinoleyloxy-3-dimethylaminopropane (DLinDMA) and derivatives thereof. Additional lipids can include, but are not limited to, 1,2-dioleoyl-sn-glycero-3-phosphoethanolamine (DOPE); cholesterol; 1,2-dioctadecanoyl-sn-glycero-3-phosphocholine (DSPC); 1,2-distearoyl-sn-glycero-3-phosphoethanolamine (DSPE). Other cationic agents can include mono- or polyaminoalkanes such as spermine and spermidine.

Cationic agents can specifically include cationic polymers. Cationic agents can also include polycation-containing cyclodextrin (for example, but not limited to, amino cyclodextrin and derivatives thereof), amino dextran, histones, protamines, cationized human serum albumin, aminopolysaccharides such as chitosan, peptides such as poly-L-lysine, poly-L-ornithine, and poly(4-hydroxy-L-proline ester, and polyamines such as polyethylenimine (PEI; available from Sigma Aldrich), polyallylamine, polypropylenimine, polyamidoamine dendrimers (PAMAM; available from Sigma Aldrich), cationic polyoxazoline and poly(beta-aminoesters). Cationic agents can also specifically include cationic lipidoids (as described by K. T. Love in the publication PNAS 107, 1864-1869 (2010)). Other exemplary cationic polymers include, but are not limited to, block copolymers such as PEG-PEI and PLGA-PEI copolymers. Other exemplary cationic agents include positively charged gelatin (for example, base-treated gelatin), and the family of aminated cucurbit[n]urils (wherein n=5, 6, 7, 8, 10).

In other embodiments of the present disclosure, cationic agents containing a portion having a positive charge in aqueous solutions at neutral pH include the following Compounds (A-I):

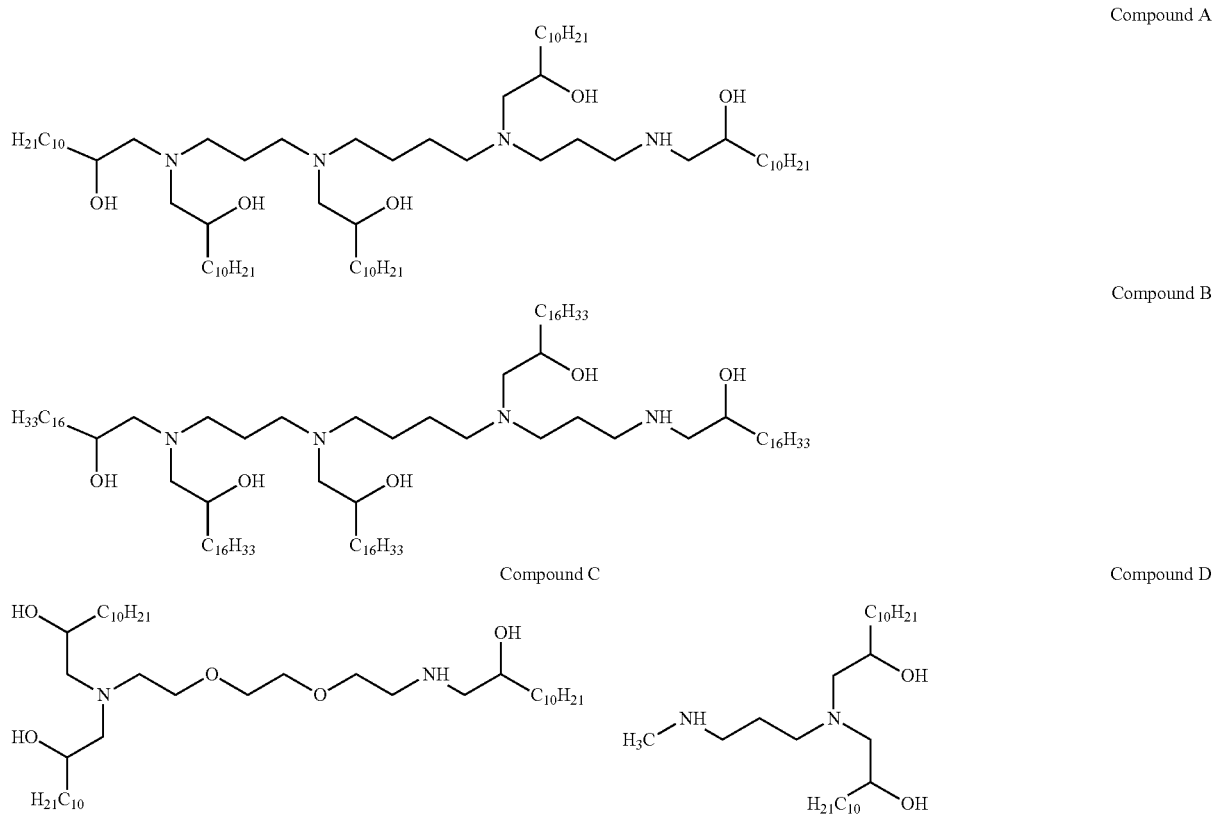

-continued

Compound E

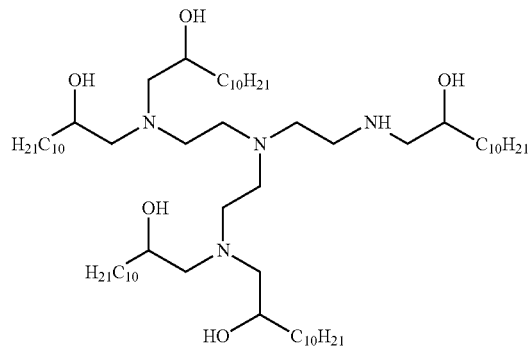

Compound F

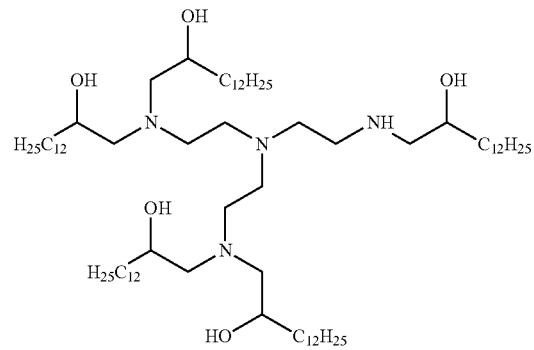

Compound G

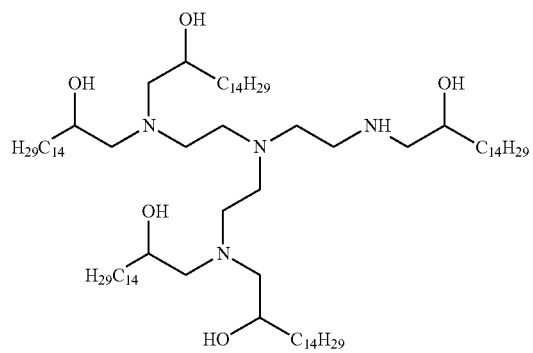

Compound H

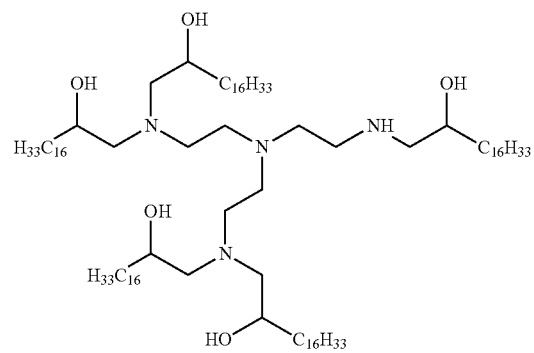

Compound I

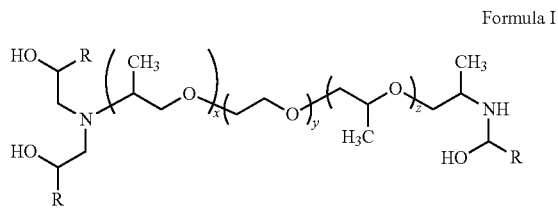

Additionally, other cationic agents include structures of the general Formula I:

Formula I

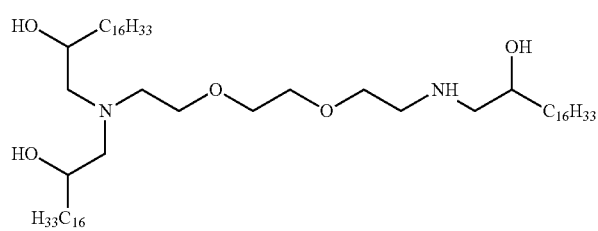

TABLE 1

Values for Variables x + z, y and R for Compounds J-R of Formula I.

| Compound | x + z | y | R |
|---|---|---|---|
| Compound J | 6 | 12.5 | $C_{12}H_{25}$ |
| Compound K | 1.2 | 2 | $C_{12}H_{25}$ |
| Compound L | 6 | 39 | $C_{12}H_{25}$ |
| Compound M | 6 | 12.5 | $C_{14}H_{29}$ |
| Compound N | 1.2 | 2 | $C_{14}H_{29}$ |

TABLE 1-continued

Values for Variables x + z, y and R for Compounds J-R of Formula I.

| Compound | x + z | y | R |
|---|---|---|---|
| Compound O | 6 | 39 | $C_{14}H_{29}$ |
| Compound P | 6 | 12.5 | $C_{16}H_{33}$ |
| Compound Q | 1.2 | 2 | $C_{16}H_{33}$ |
| Compound R | 6 | 39 | $C_{16}H_{33}$ |

Cationic agents, such as those listed above, can generally be prepared by the reaction of an appropriate hydrophobic epoxide (e.g. oleyl epoxide) with a multi-functional amine (e.g. propylene diamine). Details of the synthesis of related cationic agents are described by K. T. Love in the publication PNAS 107, 1864-1869 (2010) and Ghonaim et al., Pharma Res 27, 17-29 (2010).

It will be appreciated that polyamide derivatives of PEI (PEI-amides) can also be applied as cationic agents. PEI-amides can generally be prepared by reacting PEI with an acid or acid derivative such as an acid chloride or an ester to form various PEI-amides. For example, PEI can be reacted with methyl oleate to form PEI-amides.

In yet other embodiments cationic agents can include moieties used to condense nucleic acids (for example lipids, peptides and other cationic polymers). In some instances these cationic agents can be used to form lipoplexes and polyplexes.

Exemplary embodiments of cationic agents can also include, but are not limited to, cationic agent derivatives that are photo reactive. Photo reactive groups are described below. Such cationic agent derivatives include PEI polymer derivatives of benzophenone and PAMAM polymer derivatives of benzophenone.

In some embodiments, the molecular weight of the cationic agent can be about 1.2 kDa, 2.5 kDa, 10 kDa, 25 kDa, 250 kDa or even, in some cases, 750 kDa. In yet other embodiments the molecular weight of the cationic agent can be in the range of 50-100 kDa, 70-100 kDa, 50-250 kDa, 25-100 kDa, 2.5-750 kDa or even, in some cases, 2.5-2,000 kDa. Other embodiments include molecular weights greater than 1.2 kDa, 2.5 kDa, 10 kDa, 25 kDa, 250 kDa or even, in some cases, greater than 750 kDa. Other embodiments can include cationic agents up to 2,000 kDa.

Low molecular weight cationic agent monomers or low molecular weight cationic oligomers can be combined with hydrophobic active agent to produce a reactive coating. These reactive coatings can then be coated onto a substrate and thermally polymerized or polymerized with UV-radiation. Exemplary monomers include, but are not limited to, aziridine, vinylamine, allylamine and oligomers from 80 g/mol to 1200 g/mol. Crosslinkers (e.g., 1,2-dichloroethane, epichlorohydrin, 1,6-diisocyanatohexane) could be used to crosslink oligomers.

Additive Components

In some embodiments of the present disclosure the additive components can be hydrophilic in nature. Exemplary hydrophilic polymers include, but are not limited to, PEG, PVP and PVA.

Exemplary additive components can include saccharides. Saccharides can include monosaccharides, disaccharides, trisaccharides, oligosaccharides, and polysaccharides. Polysaccharides can be linear or branched polysaccharides. Exemplary saccharides can include but are not limited to dextrose, sucrose, maltose, mannose, trehalose, and the like. Exemplary saccharides can further include, but are not limited to, polysaccharides including pentose, and/or hexose subunits, specifically including glucans such as glycogen and amylopectin, and dextrins including maltodextrins, fructose, mannose, galactose, and the like. Polysaccharides can also include gums such as pullulan, arabinose, galactan, etc.

Saccharides can also include derivatives of polysaccharides. It will be appreciated that polysaccharides include a variety of functional groups that can serve as attachment points or can otherwise be chemically modified in order to alter characteristics of the saccharide. As just one example, it will be appreciated that saccharide backbones generally include substantial numbers of hydroxyl groups that can be utilized to derivatize the saccharide.

Saccharides can also include copolymers and/or terpolymers, and the like, that include saccharide and/or saccharide subunits and/or blocks.

Polysaccharides used with embodiments herein can have various molecular weights. By way of example, glycogen used with embodiments herein can have a molecular weight of greater than about 250,000. In some embodiments glycogen used with embodiments herein can have a molecular weight of between about 100,000 and 10,000,000 Daltons.

Refinement of the molecular weight of polysaccharides can be carried out using diafiltration. Diafiltration of polysaccharides such as maltodextrin can be carried out using ultrafiltration membranes with different pore sizes. As an example, use of one or more cassettes with molecular weight cut-off membranes in the range of about 1K to about 500 K can be used in a diafiltration process to provide polysaccharide preparations with average molecular weights in the range of less than 500 kDa, in the range of about 100 kDa to about 500 kDa, in the range of about 5 kDa to about 30 kDa, in the range of about 30 kDa to about 100 kDa, in the range of about 10 kDa to about 30 kDa, or in the range of about 1 kDa to about 10 kDa.

It will be appreciated that polysaccharides such as maltodextrin and amylose of various molecular weights are commercially available from a number of different sources. For example, Glucidex™ 6 (avg. molecular weight ~95,000 Da) and Glucidex™ 2 (avg. molecular weight ~300,000 Da) are available from Roquette (France); and MALTRIN™ maltodextrins of various molecular weights, including molecular weights from about 12,000 Da to 15,000 Da are available from GPC (Muscatine, Iowa). Examples of other hydrophobic polysaccharide derivatives are disclosed in US Patent Publication 2007/0260054 (Chudzik), which is incorporated herein by reference.

Exemplary additive components can include amphiphilic compounds. Amphiphilic compounds include those having a relatively hydrophobic portion and a relatively hydrophilic portion. Exemplary amphiphilic compounds can include, but are not limited to, polymers including, at least blocks of, polyvinylpyrrolidone, polyvinyl alcohol, polyethylene glycol, polyoxazolines (such as poly(2-alkyloxazoline) and derivatives) and the like. Exemplary amphiphilic compounds can specifically include poloxamers. Poloxamers are nonionic triblock copolymers composed of a central hydrophobic chain of polyoxypropylene flanked by two hydrophilic chains of polyoxyethylene. Poloxamers are frequently referred to by the trade name PLURONIC®. It will be appreciated that many aspects of the copolymer can be varied such the characteristics can be customized. One exemplary poloxamer is PLURONIC® F68 (nonionic, copolymer of ethylene and propylene oxide commercially available from BASF Corporation; also designated as F68 and poloxamer F68), which refers to a poloxamer having a solid form at room temperature, a polyoxypropylene molecular mass of approximately 1,800 g/mol and roughly 80% polyoxyethylene content, with a total molecular weight of approximately 8,400 g/mol, the copolymer terminating in primary hydroxyl groups.

Exemplary additive components can further include compounds that stabilize poorly water soluble pharmaceutical agents. Exemplary additive components providing such stabilization include biocompatible polymers, for example albumins. Additional additive components are described in U.S. Pat. No. 7,034,765 (De et al.), the disclosure of which is incorporated herein by reference. Stabilization of suspensions and emulsions can also be provided by compounds, for example, such as surfactants (e.g. F68).

Various additive components can be added as an optional topcoat over the layer containing the hydrophobic active agent. In some embodiments, the topcoat can be applied to modify the release characteristic of the hydrophobic active agent. Other topcoats can be added as a protection layer to reduce inadvertent loss of the hydrophobic active agent through friction or general wear. For example, the topcoat can act as a protection layer for handling purposes during packaging or to protect the hydrophobic active agent until the hydrophobic active can be delivered to the target site in the body, or both. For example, the optional topcoat can include polyvinylpyrrolidone (PVP), polyacrylic acid (PAA), and polyurethane.

Hydrophobic Active Agents

It will be appreciated that hydrophobic active agents of embodiments herein (e.g., particulate hydrophobic therapeutic agents), can include agents having many different types of activities. The terms "active agent" and "therapeutic agent" as used herein shall be coterminous unless the context dictates otherwise. Hydrophobic active agents can specifically include those having solubility in water of less than about 100 μg/mL at 25 degrees Celsius and neutral pH. In various embodiments, hydrophobic active agents can specifically include those having solubility in water of less than about 10 μg/mL at 25 degrees Celsius and neutral pH. In some embodiments, hydrophobic active agents can specifically include those having solubility in water of less than about 5 μg/ml at 25 degrees Celsius and neutral pH.

In some exemplary embodiments, active agents can include, but are not limited to, antiproliferatives such as paclitaxel, sirolimus (rapamycin), zotarolimus, everolimus, temsirolimus, pimecrolimus, tacrolimus, and ridaforolimus; analgesics and anti-inflammatory agents such as aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxyphenbutazone, phenylbutazone, piroxicam, sulindac; anti-arrhythmic agents such as amiodarone HCl, disopyramide, flecainide acetate, quinidine sulphate; anti-bacterial agents such as benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim; anti-coagulants such as dicoumarol, dipyridamole, nicoumalone, phenindione; anti-hypertensive agents such as amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCL, reserpine, terazosin HCL; anti-muscarinic agents: atropine, benzhexol HCl, biperiden, ethopropazine HCl, hyoscyamine, mepenzolate bromide, oxyphencylcimine HCl, tropicamide; anti-neoplastic agents and immunosuppressants such as aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone; beta-blockers such as acebutolol, alprenolol, atenolol, labetalol, metoprolol, nadolol, oxprenolol, pindolol, propranolol; cardiac inotropic agents such as amrinone, digitoxin, digoxin, enoximone, lanatoside C, medigoxin; corticosteroids such as beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone; lipid regulating agents such as bezafibrate, clofibrate, fenofibrate, gemfibrozil, probucol; nitrates and other anti-anginal agents such as amyl nitrate, glyceryl trinitrate, isosorbide dinitrate, isosorbide mononitrate, pentaerythritol tetranitrate.

Other exemplary embodiments of active agents include, but are not limited to, active agents for treatment of hypertension (HTN), such as guanethidine.

In a particular embodiment, the hydrophobic active agents are selected from the group consisting of paclitaxel, sirolimus (rapamycin) and mixtures thereof.

In some embodiments, a hydrophobic active agents can be conjugated to a cationic agent. The conjugation can include a hydrophobic active agent covalently bonded to the cationic agent. In some embodiments wherein the hydrophobic agent is conjugated to the cationic agent a linking agent can be used to attach the hydrophobic agent to the cationic agent. Suitable linking agents include, but are not limited to, polyethylene glycol, polyethylene oxide and polypeptides of naturally-occurring and non-naturally occurring amino acids. In some embodiments, linking agents can be biodegradable or cleavable in vivo to assist in release of the hydrophobic active agents. Exemplary linking agents can further include alkane or aromatic compounds with heteroatom-substitutions such as N, S, Si, Se or O.

Particle size and size distribution of a particulate preparation can be determined using any one of various techniques known in the art. In one mode of practice, laser diffraction can be used to measure particle size and distribution. In laser diffraction a laser beam passes through a dispersed particulate sample and angular variation in intensity of light scattered is measured. The angle of light scattering is greater for large particles and less for smaller particles, and the angular scattering intensity data can be collected and analyzed to generate a particle size profile.

Analysis of particulate size and distribution can be performed using laser light scattering equipment such as Malvern System 4700, (for particles from 1 nm to 3 μm) or Horiba LA-930 (e.g., for particles from 100 nm to 2 mm). The output from such analyzers can provide information on the sizes of individual particulates, and the overall amount of particulates of these sizes reflecting the distribution of particulates in terms of size. Analysis providing data on the size distribution can be provided in the form of a histogram, graphically representing the size and size distribution of all the particulates in a preparation.

Exemplary particulate hydrophobic therapeutic agents can have different morphological characteristics. In some embodiments the particulate hydrophobic therapeutic agent can be crystalline. In yet other embodiments of the present disclosure the particulate hydrophobic therapeutic agent can be amorphous. Additionally, combinations of crystalline and amorphous particulate hydrophobic therapeutic agents can be desirable in order to achieve, for example, desired solubilities of the particulate hydrophobic therapeutic agents.

In some embodiments, the particulate hydrophobic therapeutic agent can have an average diameter ("dn", number average) that is less than about 30 μm or less than about 10 μm. Also, in some embodiments, the particulate hydrophobic therapeutic agent can have an average diameter of about 100 nm or larger. For example, the microparticulates associated with the expandable elastic portion can have an average diameter in the range of about 100 nm to about 10 μm, about 150 nm to about 2 μm, about 200 nm to about 5 μm, or even about 0.3 μm to about 1 μm.

Nucleic Acids

Nucleic acids used with embodiments of the invention can include various types of nucleic acids that can function to provide a therapeutic effect. Exemplary types of nucleic acids can include, but are not limited to, ribonucleic acids (RNA), deoxyribonucleic acids (DNA), small interfering RNA (siRNA), micro RNA (miRNA), piwi-interacting RNA (piRNA), short hairpin RNA (shRNA), antisense nucleic acids, aptamers, ribozymes, locked nucleic acids and catalytic DNA. In a particular embodiment, the nucleic acid used is siRNA and/or derivatives thereof.

In some exemplary embodiments of the present disclosure, the range of the percent ratio of hydrophobic active agent to cationic agent (e.g. % PTX/% PEI or % PTX/% DOTAP; wt/wt) is from about 99.9/0.1 to about 70/30. In yet other embodiments it can be appreciated that the range of the percent ratio of hydrophobic active agents is from about 99/1 to about 73/27; from about 98/2 to about 75/25; from about 98/2 to about 86/14; from about 97/3 to about 88/12; from about 95/5 to about 90/10; and even in some exemplary embodiments from about 93/7 to about 91/9.

Hydrophilic Base Coatings

In various embodiments herein, a hydrophilic base coat and/or the substrate of the device or a portion of the device can be formed from a hydrophilic material such as a hydrophilic polyether block amide copolymer. The polyether block amide copolymer can include blocks with hydrophilic properties. In some embodiments the polyether block amide copolymer can include blocks of polyethylene glycol (PEG).

In various embodiments, the hydrophilic polyether block amide copolymer can have a water contact angle less than or equal to 80 degrees. In various embodiments, the hydrophilic polyether block amide copolymer can have a water contact angle less than or equal to 70 degrees. In various embodiments, the hydrophilic polyether block amide copolymer can have a water contact angle less than or equal to 60 degrees. In some embodiments, the hydrophilic polyether block amide copolymer can have a water contact angle greater than or equal to 20 degrees.

In some embodiments the hydrophilic polyether block amide copolymer can have a water absorption at equilibrium at 20 degrees Celsius and 50% relative humidity of greater than or equal to 1.0, 1.1, 1.2, 1.3, 1.4, 1.5, or 1.6% (as measured by ISO 62). In some embodiments the hydrophilic polyether block amide copolymer can have a water absorption at equilibrium at 20 degrees Celsius and 50% relative humidity of less than 5.0, 4.5, 4.0, 3.5, 3.0, 2.5, 2.0 or 1.6% (as measured by ISO 62).

Exemplary hydrophilic polyether block amide copolymers include PEBAX® MV1074 and MI-11657, commercially available from Arkema. Some examples of hydrophilic polyether block amide copolymers are described in U.S. Pat. No. 8,952,103 and U.S. Publ. Pat. Appl. No. US2009/0221767 the content of which relating to hydrophilic polyether block amide copolymers is herein incorporated by reference.

Substrates

In embodiments the device substrate can be formed from a hydrophilic polyether block amide copolymer such as those described above. However, in some embodiments the hydrophilic polyether block amide copolymer does not form the substrate, but exists as a layer disposed over the substrate. In such embodiments it will be appreciated that the substrate can be formed from any desirable material, or combination of materials, suitable for use within the body. In some embodiments the substrate is formed from compliant and flexible materials, such as elastomers (polymers with elastic properties). Exemplary elastomers can be formed from various polymers including polyurethanes and polyurethane copolymers, polyethylene, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, polyether-polyamide copolymers, and the like. The substrate can be made of a single elastomeric material, or a combination of materials.

Other materials for the substrate can include those formed of polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone.

Beyond polymers, and depending on the type of device, the substrate can also be formed of other inorganic materials such as metals (including metal foils and metal alloys), glass and ceramics.

Processes to modify substrates described above can include chemical modifications to improve performance characteristics of the substrate. Specific chemical processes that can be used include ozone treatment, chemical oxidation, acid chemical etching, base chemical etching, plasma treatment and corona treatment, surface grafting, thermally activated coating processes (both covalent and non-covalent) and surface modifications including coatings containing dopamine, tannic acid, plant polyphenols and other catechols or catechol containing derivatives of hydrophilic moieties. Additionally, processes to form substrates described above can include physical modifications for example, but not limited to, sand blasting and surface texturing (for example either during or after the molding process of polymers).

In some embodiments, the modification of substrates as described herein can allow for omission of a base coating layer (such as a hydrophilic layer) as substrate surfaces that have been modified will allow for improved adhesion of a hydrophobic therapeutic agent and cationic agent compared with that of a hydrophilic layer.

Devices

It will be appreciated that embodiments herein include, and can be used in conjunction with, various types of devices including, but not limited to, drug delivery devices such as drug eluting balloon catheters, drug-containing balloon catheters, stents, grafts, and the like.

Some embodiments described herein can be used in conjunction with balloon expandable flow diverters, and self-expanding flow diverters. Other embodiments can include uses in contact with angioplasty balloons (for example, but not limited to, percutaneous transluminal coronary angioplasty and percutaneous transluminal angioplasty). Yet other embodiments can include uses in conjunction with sinoplasty balloons for ENT treatments, urethral balloons and urethral stents for urological treatments and gastro-intestinal treatments (for example, devices used for colonoscopy). Hydrophobic active agent can be transferred to tissue from a balloon-like inflatable device or from a patch-like device. Other embodiments of the present disclosure can further be used in conjunction with micro-infusion catheter devices. In some embodiments, micro-infusion catheter devices can be used to target active agents to the renal sympathetic nerves to treat, for example, hypertension.

Embodiments included herein can also be used in conjunction with the application of various active agents to the skin (for example, but not limited to transdermal drug delivery).

Other exemplary medical applications wherein embodiments of the present disclosure can be used further encompass treatments for bladder neck stenosis (e.g. subsequent to transurethral resection of the prostrate), laryngotrachial stenosis (e.g. in conjunction with serial endoscopic dilatation to treat subglottic stenosis, treatment of oral cancers and cold sores and bile duct stenosis (e.g. subsequent to pancreatic, hepatocellular of bile duct cancer). By way of further example, embodiments herein can be used in conjunction with drug applicators. Drug applicators can include those for use with various procedures, including surgical procedures, wherein active agents need to be applied to specific tissue locations. Examples can include, but are not limited to, drug applicators that can be used in orthopedic surgery in order to apply active agents to specific surfaces of bone, cartilage, ligaments, or other tissue through physical contact of the drug applicator with those tissues. Drug applicators can include, without limitation, hand-held drug applicators, drug patches, drug stamps, drug application disks, and the like.

In some embodiments, drug applicators can include a surface having a hydrophilic polymer layer disposed thereon and coated therapeutic agent particles disposed on the hydrophilic polymer layer, the coated therapeutic agent particles comprising a particulate hydrophobic therapeutic agent; and a cationic agent disposed over the particulate hydrophobic therapeutic agent.

In use, various embodiments included herein can enable rapid transfer of therapeutic agents to specific targeted tissues. For example, in some embodiments, a care provider can create physical contact between a portion of a drug delivery device including a therapeutic agent and the tissue being targeted and the therapeutic agent will be rapidly transferred from the drug delivery device to that tissue. As such, precise control over which tissues the therapeutic agent is provided to can be achieved.

One beneficial aspect of various embodiments described herein is that the therapeutic agent can be transferred from the drug delivery device or coating to the targeted tissue very rapidly. In some embodiments substantial transfer of the therapeutic agent from the drug delivery device or coating to the tissue occurs in 30 minutes or less. In some embodiments substantial transfer of the therapeutic agent from the drug delivery device or coating to the tissue occurs in 15 minutes or less. In some embodiments substantial transfer of the therapeutic agent from the drug delivery device or coating to the tissue occurs in 10 minutes or less. In some embodiments substantial transfer of the therapeutic agent from the drug delivery device or coating to the tissue occurs in 5 minutes or less. In some embodiments substantial transfer of the therapeutic agent from the drug delivery device or coating to the tissue occurs in 2 minutes or less. In some embodiments substantial transfer of the therapeutic agent from the drug delivery device or coating to the tissue occurs in 1 minute or less.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference. To the extent inconsistencies arise between publications and patent applications incorporated by reference and the present disclosure, information in the present disclosure will govern.

The invention has been described with reference to various specific and preferred embodiments and techniques. However, it should be understood that many variations and modifications may be made while remaining within the spirit and scope of the invention.

The invention claimed is:

1. A drug delivery coating for an inflatable balloon comprising
  a base polymeric layer, the base polymeric layer comprising a hydrophilic polyether block amide copolymer and having a hydrophilic surface, the base polymeric layer configured to be disposed on the inflatable balloon;
  a therapeutic agent layer forming an exterior surface of the drug delivery coating, the therapeutic agent layer disposed on the hydrophilic surface of the base polymeric layer and having a composition different than the base polymeric layer, the therapeutic agent layer comprising
    a particulate hydrophobic therapeutic agent; and
    a cationic agent;
  wherein the therapeutic agent layer is configured on the exterior surface to be transferred from the hydrophilic surface to a target tissue in 15 minutes or less.

2. The drug delivery coating of claim 1, the hydrophilic polyether block amide copolymer having a water contact angle less than or equal to 80 degrees.

3. The drug delivery coating of claim 1, the hydrophilic polyether block amide copolymer having a water contact angle less than or equal to 70 degrees.

4. The drug delivery coating of claim 1, the hydrophilic polyether block amide copolymer having a water contact angle less than or equal to 60 degrees.

5. The drug delivery coating of claim 1, the hydrophilic polyether block amide copolymer comprising a water absorption at equilibrium at 20 degrees Celsius and 50% relative humidity of greater than 1.0% (ISO 62).

6. The drug delivery coating of claim 1, the hydrophilic polyether block amide copolymer comprising a water absorption at equilibrium at 20 degrees Celsius and 50% relative humidity of 1.4% or greater (ISO 62).

7. The drug delivery coating of claim 1, the particulate hydrophobic therapeutic agent and the cationic agent forming coated therapeutic agent particles.

8. The drug delivery coating of claim 1, the cationic agent selected from the group consisting of cationic lipids, neutral lipids with cationic groups, and cationic polymers.

9. The drug delivery coating of claim 1, the cationic agent selected from the group consisting of polyethyleneimine and 1,2-dioleoyl-3-trimethylammonium-propane (DOTAP).

10. A drug delivery device comprising a drug delivery coating for an inflatable balloon, the drug delivery device comprising a substrate comprising the inflatable balloon;
- a base polymeric layer, the base polymeric layer comprising a hydrophilic polyether block amide copolymer and having a hydrophilic surface, the base polymeric layer configured to be disposed on the inflatable balloon;
- a therapeutic agent layer forming an exterior surface of at least a portion of the drug delivery device, the therapeutic agent layer contacting the hydrophilic surface of the substrate, the therapeutic agent layer comprising
- a particulate hydrophobic therapeutic agent; and
- a cationic agent; and
- wherein the therapeutic agent layer is configured on the exterior surface to be transferred from the hydrophilic surface to a target tissue in 15 minutes or less.

11. The drug delivery device of claim 10, the hydrophilic polyether block amide copolymer having a water contact angle less than or equal to 80 degrees.

12. The drug delivery device of claim 10, the hydrophilic polyether block amide copolymer comprising a water absorption at equilibrium at 20 degrees Celsius and 50% relative humidity of greater than 1.0% (ISO 62).

13. A method of making a medical device comprising a drug delivery coating for an inflatable balloon, the method comprising:
- depositing a base polymeric layer onto at least a portion of the inflatable balloon,
- the base polymeric layer comprising a hydrophilic polyether block amide copolymer and having a hydrophilic surface, the base polymeric layer configured to be disposed on the inflatable balloon;
- depositing a therapeutic agent layer onto at least a portion of the base polymeric layer, the therapeutic agent layer contacting the surface of the base polymeric layer, the therapeutic agent layer comprising
- a particulate hydrophobic therapeutic agent; and
- a cationic agent; and
- wherein the therapeutic agent layer is configured on the exterior surface to be transferred from the hydrophilic surface to a target tissue in 15 minutes or less.

14. The method of claim 13, the hydrophilic polyether block amide copolymer having a water contact angle less than or equal to 80 degrees.

15. The method of claim 13, the hydrophilic polyether block amide copolymer comprising a water absorption at equilibrium at 20 degrees Celsius and 50% relative humidity of greater than 1.0% (ISO 62).

16. The method of claim 13, wherein the therapeutic agent layer is deposited using a solvent that does not absorb into the hydrophilic polyether block amide copolymer.

17. A drug delivery coating for an inflatable balloon comprising
- a base polymeric layer, the base polymeric layer comprising a hydrophilic polyether block amide copolymer and having a hydrophilic surface, the base polymeric layer configured to be disposed on the inflatable balloon;
- a therapeutic agent layer forming an exterior surface of the drug delivery coating, the therapeutic agent layer disposed on the hydrophilic surface of the base polymeric layer and having a composition different than the base polymeric layer, the therapeutic agent layer comprising
- a particulate hydrophobic therapeutic agent; and
- a cationic agent;
- wherein the therapeutic agent layer is configured on the exterior surface for delivery to a cell membrane and cellular components within a lipid bilayer in 5 minutes or less.

18. The drug delivery coating of claim 1, the hydrophilic polyether block amide copolymer having a water contact angle less than or equal to 20 degrees.

* * * * *